US012700496B2

(12) United States Patent
Synghal et al.

(10) Patent No.: US 12,700,496 B2
(45) Date of Patent: Aug. 4, 2026

(54) AUGMENTING HEALTHCARE STEWARDSHIP USING MACHINE LEARNING

(71) Applicant: Kaiser Foundation Hospitals, Oakland, CA (US)

(72) Inventors: Rajiv K. Synghal, Pleasanton, CA (US); Hovannes Daniels, Huntington Beach, CA (US); Ramanbir Jaj, Dublin, CA (US); Pradeep Chowdhury, Dublin, CA (US); Jonathan King, Sacramento, CA (US)

(73) Assignee: Kaiser Foundation Health Plan, Inc., Oakland, CA (US)

( * ) Notice: Subject to any disclaimer, the term of this patent is extended or adjusted under 35 U.S.C. 154(b) by 0 days.

(21) Appl. No.: 19/096,497

(22) Filed: Mar. 31, 2025

(65) Prior Publication Data
US 2025/0372241 A1 Dec. 4, 2025

Related U.S. Application Data

(60) Provisional application No. 63/654,686, filed on May 31, 2024.

(51) Int. Cl.
| | |
|---|---|
| *G16H 40/00* | (2018.01) |
| *G16H 20/00* | (2018.01) |
| *G16H 40/20* | (2018.01) |
| *G16H 50/70* | (2018.01) |

(52) U.S. Cl.
CPC ............. *G16H 40/20* (2018.01); *G16H 20/00* (2018.01); *G16H 50/70* (2018.01)

(58) Field of Classification Search
CPC ........ G16H 40/20; G16H 50/70; G16H 20/00; G16H 20/10; G06F 3/0482; G06F 3/04847
USPC ....................................................... 705/2, 3
See application file for complete search history.

(56) References Cited

U.S. PATENT DOCUMENTS

| | | | |
|---|---|---|---|
| 2015/0095067 A1* | 4/2015 | Ryan ...................... | G16H 20/13 |
| | | | 705/3 |
| 2015/0269348 A1* | 9/2015 | Madjd ................... | G16H 50/30 |
| | | | 705/2 |
| 2016/0151015 A1* | 6/2016 | Condurso .............. | A61B 5/002 |
| | | | 705/2 |
| 2021/0177339 A1* | 6/2021 | Colorafi ................ | A61B 5/412 |
| 2022/0391735 A1* | 12/2022 | Platt ...................... | G16H 40/20 |
| 2024/0257928 A1* | 8/2024 | Harnach ............... | G16H 50/20 |
| 2024/0257931 A1* | 8/2024 | Ginsburg .............. | G16H 20/10 |
| 2025/0037828 A1* | 1/2025 | Ambrose ............... | G16H 70/20 |

(Continued)

*Primary Examiner* — Alaaeldin M. Elshaer
(74) *Attorney, Agent, or Firm* — Patent Law Works, LLP

(57) ABSTRACT

A system and method for facilitating a member journey through healthcare service by augmenting stewardship workflow across multiple service areas is disclosed. The system and method includes augmenting the healthcare stewardship workflow by standardizing the healthcare service practices, increasing the quality of care for patients, improving the workflow efficiency of healthcare personnel, reducing the costs associated with providing healthcare services, and enabling the ease of regulatory compliance using machine learning techniques. The system and method provides the healthcare personnel with access to healthcare-relevant and fact-based artificial intelligence powered by machine learning for decision support opportunities to drive recommended care pathways.

20 Claims, 19 Drawing Sheets

(56) References Cited

U.S. PATENT DOCUMENTS

| | | | |
|---|---|---|---|
| 2025/0201373 A1* | 6/2025 | Williams | ............... G16H 20/10 |
| 2025/0259715 A1* | 8/2025 | Crabtree | ................ G16C 20/80 |

* cited by examiner

Figure 4:
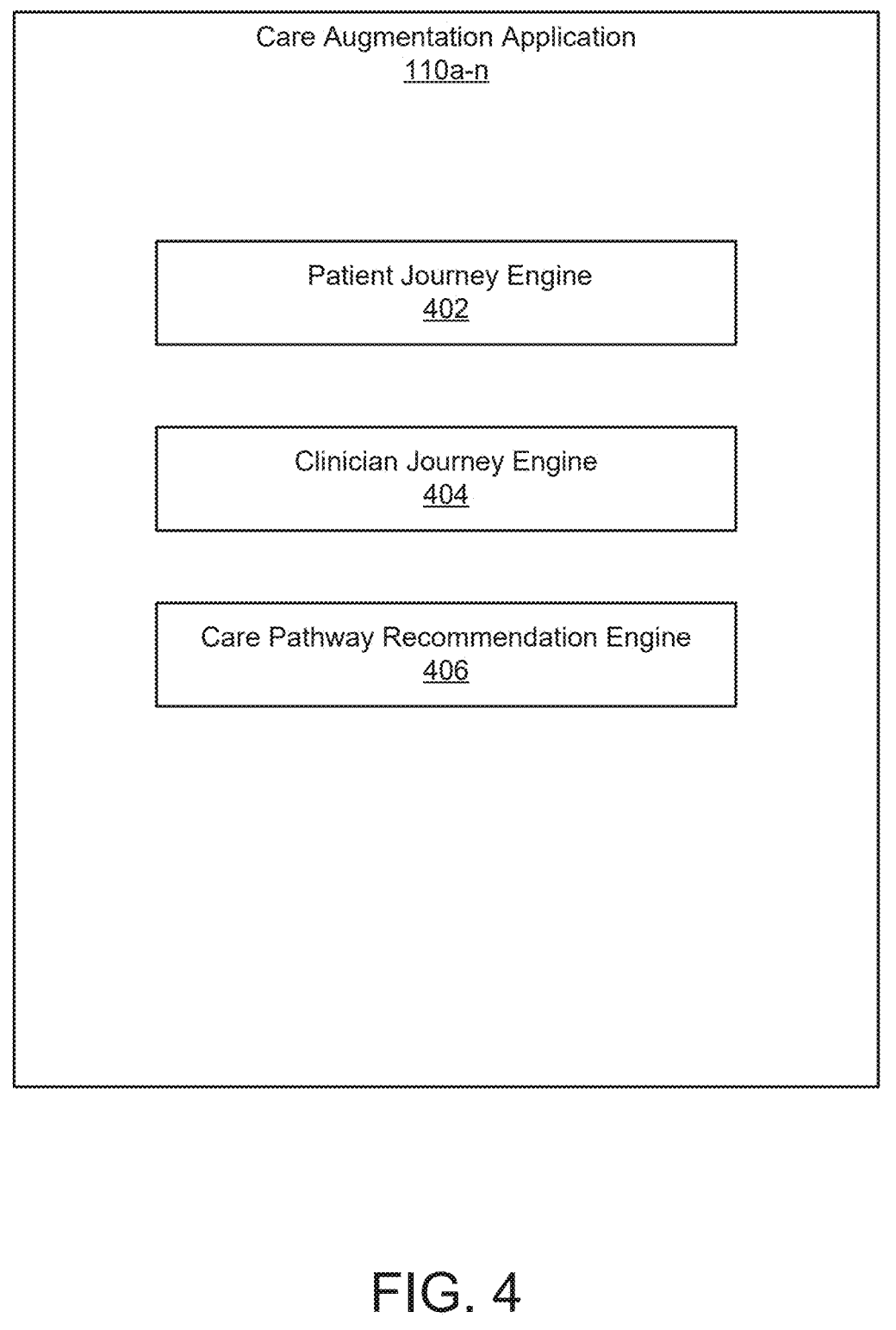

Care Augmentation Application
110a-n

Patient Journey Engine
402

Clinician Journey Engine
404

Care Pathway Recommendation Engine
406

Figure 12:
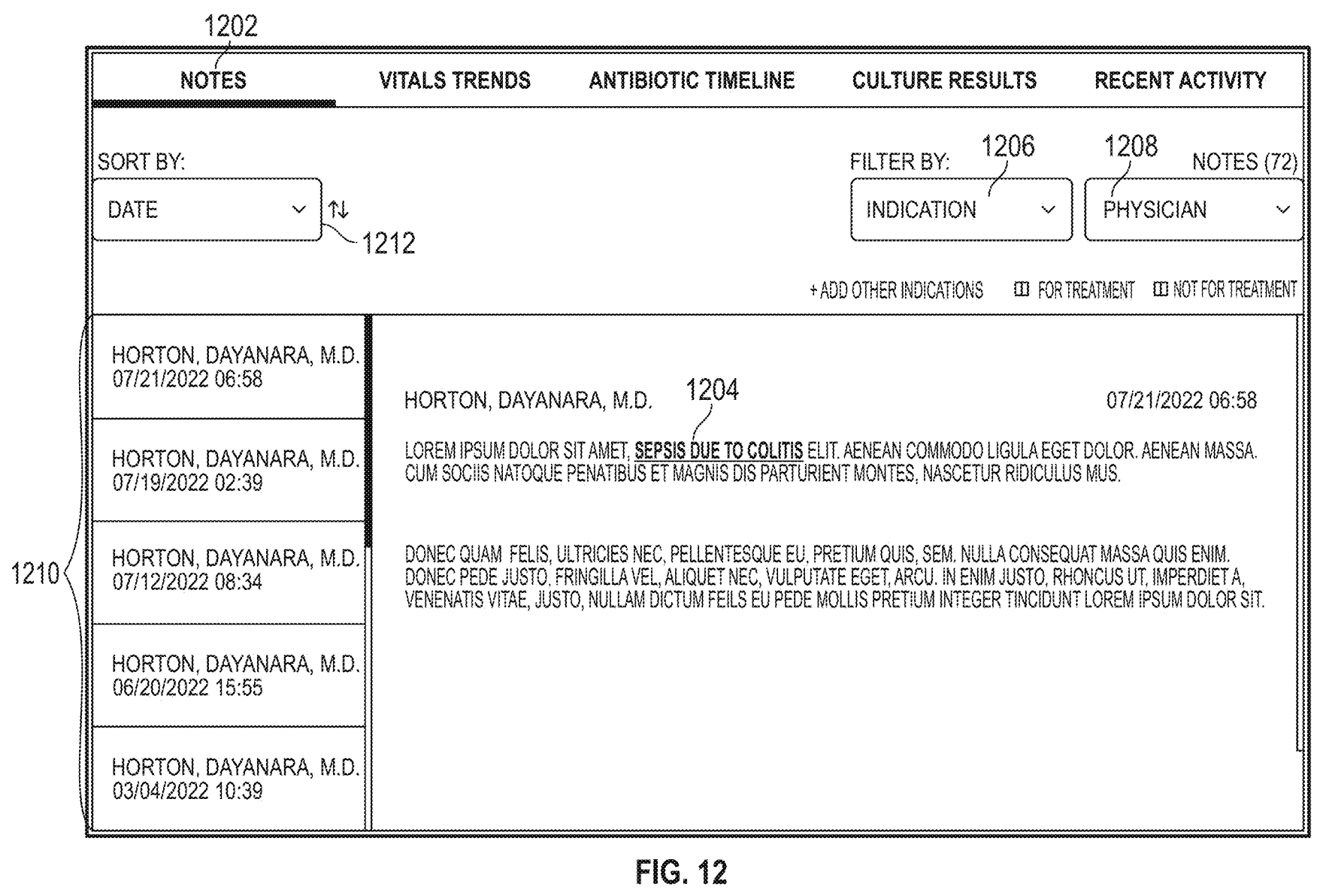

NOTES    VITALS TRENDS    ANTIBIOTIC TIMELINE    CULTURE RESULTS    RECENT ACTIVITY

1202

SORT BY:

DATE    ⌄    ⇅
1212

FILTER BY:    1206    1208    NOTES (72)

INDICATION    ⌄    PHYSICIAN    ⌄

+ ADD OTHER INDICATIONS    ▣ FOR TREATMENT    ▣ NOT FOR TREATMENT

HORTON, DAYANARA, M.D.    1204
07/21/2022 06:58

LOREM IPSUM DOLOR SIT AMET, SEPSIS DUE TO COLITIS ELIT. AENEAN COMMODO LIGULA EGET DOLOR. AENEAN MASSA.
CUM SOCIIS NATOQUE PENATIBUS ET MAGNIS DIS PARTURIENT MONTES, NASCETUR RIDICULUS MUS.

DONEC QUAM FELIS, ULTRICIES NEC, PELLENTESQUE EU, PRETIUM QUIS, SEM. NULLA CONSEQUAT MASSA QUIS ENIM.
DONEC PEDE JUSTO, FRINGILLA VEL, ALIQUET NEC, VULPUTATE EGET, ARCU. IN ENIM JUSTO, RHONCUS UT, IMPERDIET A,
VENENATIS VITAE, JUSTO. NULLAM DICTUM FELIS EU PEDE MOLLIS PRETIUM INTEGER TINCIDUNT LOREM IPSUM DOLOR SIT.

07/21/2022 06:58

HORTON, DAYANARA, M.D.
07/21/2022 06:58

HORTON, DAYANARA, M.D.
07/19/2022 02:39

HORTON, DAYANARA, M.D.
07/12/2022 08:34

HORTON, DAYANARA, M.D.
06/20/2022 15:55

HORTON, DAYANARA, M.D.
03/04/2022 10:39

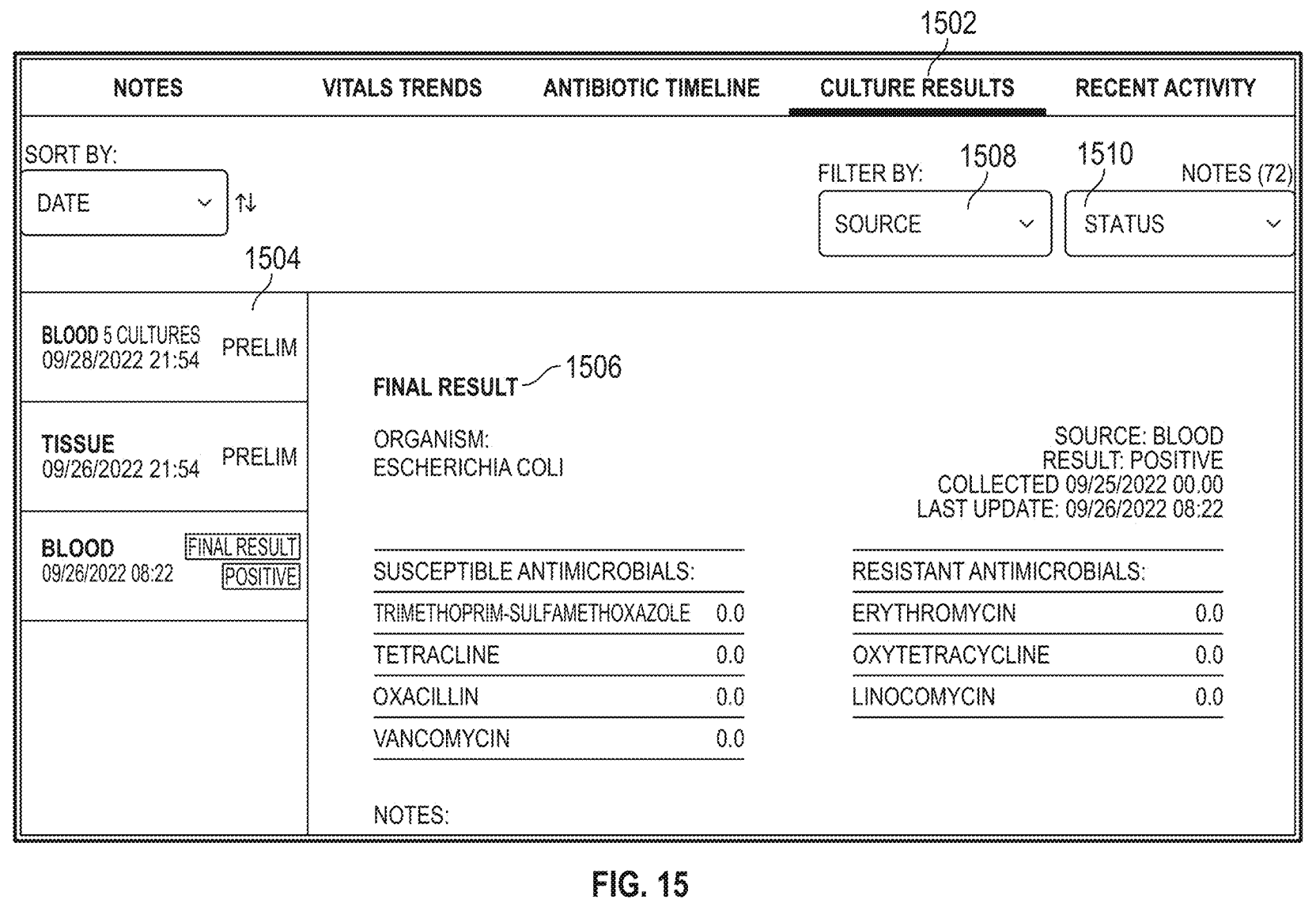

| NOTES | VITALS TRENDS | ANTIBIOTIC TIMELINE | CULTURE RESULTS | RECENT ACTIVITY |

SORT BY:

DATE ⌄  ⇅

1504

FILTER BY: 1508    1510

SOURCE ⌄    STATUS ⌄

NOTES (72)

BLOOD 5 CULTURES    PRELIM
09/28/2022 21:54

TISSUE    PRELIM
09/26/2022 21:54

BLOOD    FINAL RESULT  POSITIVE
09/26/2022 08:22

FINAL RESULT ⟋ 1506

ORGANISM:
ESCHERICHIA COLI

SOURCE: BLOOD
RESULT: POSITIVE
COLLECTED 09/25/2022 00:00
LAST UPDATE: 09/26/2022 08:22

| SUSCEPTIBLE ANTIMICROBIALS: | | RESISTANT ANTIMICROBIALS: | |
|---|---|---|---|
| TRIMETHOPRIM-SULFAMETHOXAZOLE | 0.0 | ERYTHROMYCIN | 0.0 |
| TETRACLINE | 0.0 | OXYTETRACYCLINE | 0.0 |
| OXACILLIN | 0.0 | LINOCOMYCIN | 0.0 |
| VANCOMYCIN | 0.0 | | |

NOTES:

FIG. 15

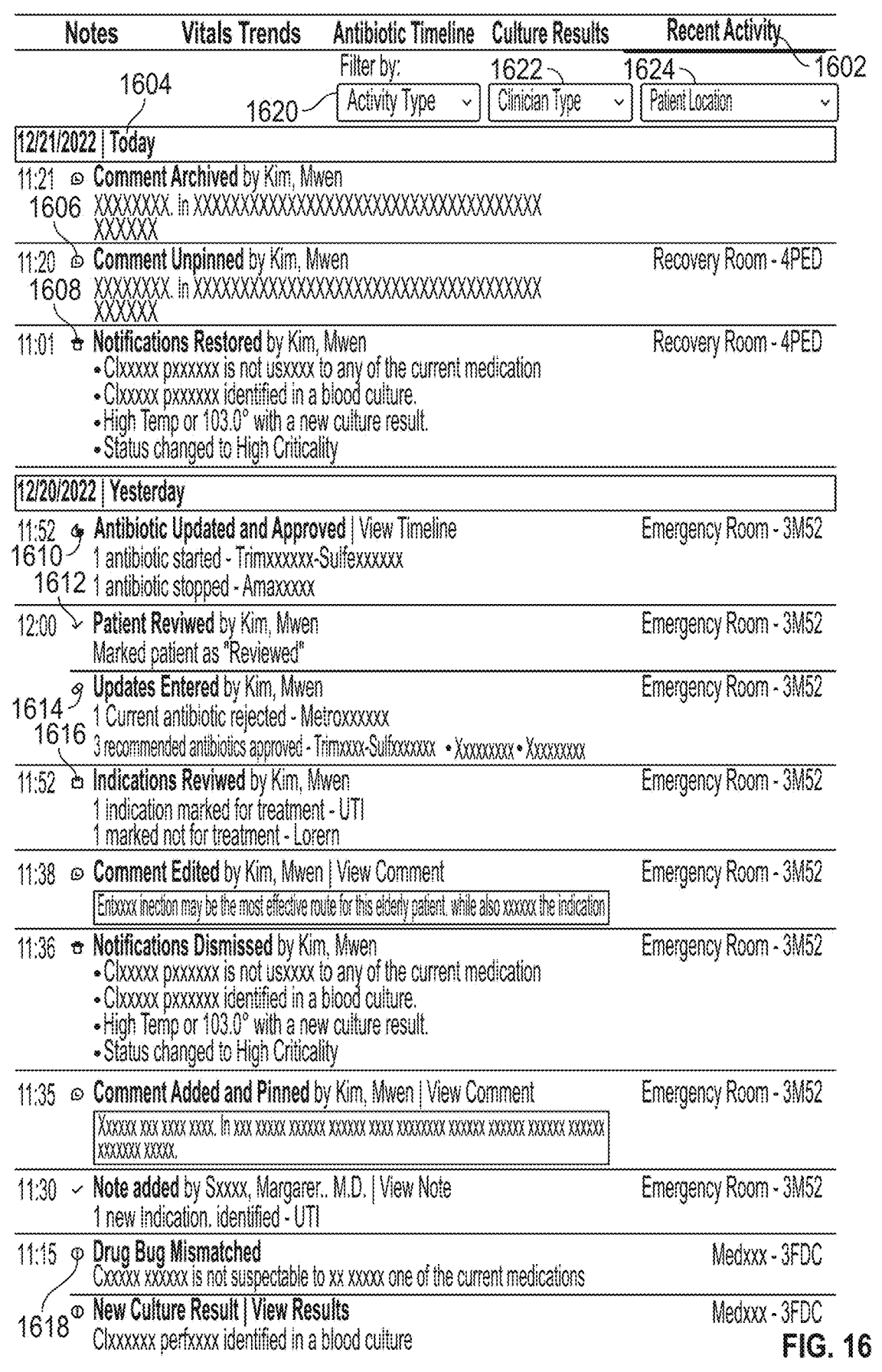

| Notes | Vitals Trends | Antibiotic Timeline | Culture Results | Recent Activity |

Filter by:    1622    1624    1602

1620    | Activity Type ▾ | Clinician Type ▾ | Patient Location ▾ |

1604

12/21/2022 | Today

11:21 ☺ Comment Archived by Kim, Mwen
1606  XXXXXXXX. in XXXXXXXXXXXXXXXXXXXXXXXXXXXXXXXXXX
XXXXXX 11:20 ☺ Comment Unpinned by Kim, Mwen                    Recovery Room - 4PED
1608  XXXXXXXX. in XXXXXXXXXXXXXXXXXXXXXXXXXXXXXXXXXX
XXXXXX 11:01 ☺ Notifications Restored by Kim, Mwen              Recovery Room - 4PED
• Clxxxxx pxxxxxx is not usxxxx to any of the current medication
• Clxxxxx pxxxxxx identified in a blood culture.
• High Temp or 103.0° with a new culture result.
• Status changed to High Criticality

12/20/2022 | Yesterday

11:52 ☺ Antibiotic Updated and Approved | View Timeline    Emergency Room - 3M52
1610  1 antibiotic started - Trimxxxxxx-Sulfexxxxxx
1612  1 antibiotic stopped - Amaxxxxx 12:00 ☺ Patient Reviewed by Kim, Mwen                     Emergency Room - 3M52
Marked patient as "Reviewed"

1614 ☺ Updates Entered by Kim, Mwen                      Emergency Room - 3M52
1 Current antibiotic rejected - Metroxxxxxx
1616  3 recommended antibiotics approved - Trimxxxx-Sulfxxxxxx • Xxxxxxxx • Xxxxxxxx 11:52 ☺ Indications Reviewed by Kim, Mwen                Emergency Room - 3M52
1 indication marked for treatment - UTI
1 marked not for treatment - Lorem 11:38 ☺ Comment Edited by Kim, Mwen | View Comment       Emergency Room - 3M52
| Enbxxxx inection may be the most effective route for this elderly patient. while also xxxxxx the indication |

11:36 ☺ Notifications Dismissed by Kim, Mwen             Emergency Room - 3M52
• Clxxxxx pxxxxxx is not usxxxx to any of the current medication
• Clxxxxx pxxxxxx identified in a blood culture.
• High Temp or 103.0° with a new culture result.
• Status changed to High Criticality 11:35 ☺ Comment Added and Pinned by Kim, Mwen | View Comment    Emergency Room - 3M52
| Xxxxxx xxx xxxx xxxx. In xxx xxxxx xxxxxx xxxxxx xxxx xxxxxxxx xxxxxx xxxxxx xxxxxx xxxxxx
xxxxxx xxxxx. |

11:30 ☺ Note added by Sxxxx, Margarer.. M.D. | View Note    Emergency Room - 3M52
1 new Indication. identified - UTI 11:15 ☺ Drug Bug Mismatched                             Medxxx - 3FDC
Cxxxxx xxxxxx is not suspectable to xx xxxxxx one of the current medications 1618 ☺ New Culture Result | View Results                Medxxx - 3FDC
Clxxxxxx perfxxxx identified in a blood culture

FIG. 16

EMPIRIC RECOMMENDATIONS ⟋ 1706

✓  ✗  TRIMETHPRIM-SULFAMEXXXXXXX    INDICATIONS: PNEUMONIA

✓  ✗  METROPEREM    INDICATIONS: UTI
                     ALLERGY: PENICILLIN (LOW)

+ ADD ANTIBIOTIC ⟋ 1708

COMMENT (OPTIONAL)

ENTER COMMENT

FURTHER REVIEW  ◉ NONE   ○ PHYSICIAN   ○ ID PANEL

⟋ 1712

CANCEL    SUBMIT

1710 ⟋

RESISTANT
CIPROFLEXACIN                                          0.02
XXXXXXXXXXXX                                           1

PROTOUS MIRABILIS
SUCCEPTIBLE
XXXXXXXXX XXX.XX XXXXXX XXX                            0.006
XXXXXXXX XXXXXXXX                                      0.006
CIPROFLEXACIN                                          0.006
GERMANCIN                                              0.006
RESISTANT
XXXXXXXXXXX                                            0.006

02/27/2022 00:00

URINE
09/23/2022 00:00

GLOSTRIDUM PERFINGERS
...
SUCCEPTIBLE
GERMANCIN                                              0.006
CIPROFLEXACIN                                          0.006
RESISTANT
XXXXXXXXXXXX                                           0.006

⟋ 1718

PRELIMINARY RESULTS (2)                               ‹

STERILE
09/21/2022 00:00
RESULT PENDING

FIG. 17
(Continued)

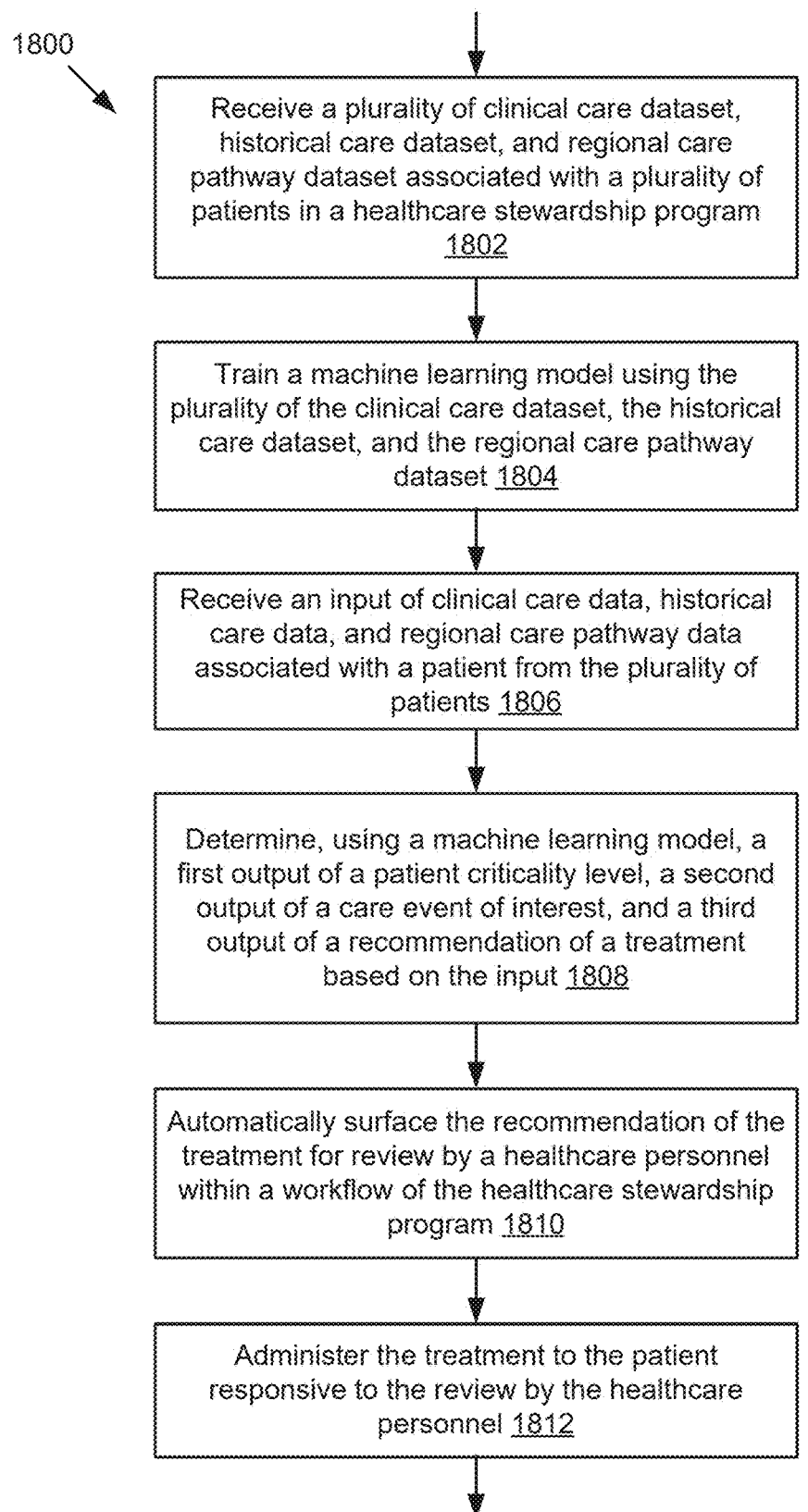

1800

Receive a plurality of clinical care dataset, historical care dataset, and regional care pathway dataset associated with a plurality of patients in a healthcare stewardship program 1802

Train a machine learning model using the plurality of the clinical care dataset, the historical care dataset, and the regional care pathway dataset 1804

Receive an input of clinical care data, historical care data, and regional care pathway data associated with a patient from the plurality of patients 1806

Determine, using a machine learning model, a first output of a patient criticality level, a second output of a care event of interest, and a third output of a recommendation of a treatment based on the input 1808

Automatically surface the recommendation of the treatment for review by a healthcare personnel within a workflow of the healthcare stewardship program 1810

Administer the treatment to the patient responsive to the review by the healthcare personnel 1812

FIG.18

AUGMENTING HEALTHCARE STEWARDSHIP USING MACHINE LEARNING

CROSS REFERENCE TO RELATED APPLICATIONS

This application claims the benefit of U.S. Provisional Patent Application No. 63/654,686, titled "Healthcare Stewardship using Machine Learning," filed May 31, 2024, the entire contents of which are herein incorporated by reference.

BACKGROUND

This specification generally relates to facilitating a member journey through one or more touchpoints of a healthcare stewardship workflow. In particular, the specification relates to a system and method for augmenting the healthcare stewardship workflow by standardizing the healthcare service practices, increasing the quality of care for patients, improving the workflow efficiency of healthcare personnel, reducing the costs associated with providing healthcare services, and enabling the ease of regulatory compliance using machine learning techniques.

Typically healthcare related entities, such as healthcare organizations, healthcare providers, physician offices, pharmacies, laboratories, and hospitals continuously handle thousands of patient-entity interactions per day at different geographical locations. The nature and reason for these patient-entity interactions vary significantly and can be anything ranging from treating mundane to serious illness associated with the patient. One issue is that providing the healthcare stewardship across multiple service areas is often time and labor intensive for the healthcare personnel. Another issue is the increasing cognitive burden on the healthcare personnel that has serious implications on patient safety and quality of care. Furthermore, there is an increasing demand to reduce patient treatment time and associated healthcare spending costs, facilitate efficient utilization of healthcare provider skills and resources to improve patient experience and satisfaction, and optimize different care coordination and delivery workflows in a healthcare stewardship program while meeting healthcare compliance, quality of patient care, patient safety requirements.

This background description provided herein is for the purpose of generally presenting the context of the disclosure.

SUMMARY

The techniques introduced herein overcome the deficiencies and limitations of the prior art at least in part by providing systems and methods for augmenting the healthcare stewardship workflow.

According to one innovative aspect of the subject matter described in this disclosure, a method includes: receiving a plurality of clinical care dataset, historical care dataset, and regional care pathway dataset associated with a plurality of patients in a healthcare stewardship program; training a machine learning model using the plurality of the clinical care dataset, the historical care dataset, and the regional care pathway dataset, the plurality of the clinical care dataset, the historical care dataset, and the regional care pathway dataset including known care events of interest, patient criticality levels, and patient care treatments to train the machine learning model; receiving an input of clinical care data, historical care data, and regional care pathway data associated with a patient from the plurality of patients; determining, using the machine learning model, a first output of a patient criticality level, a second output of a care event of interest associated with the patient criticality level, and a third output of a recommendation of a treatment associated with the patient criticality level and the care event of interest based on the input of the clinical care data, the historical care data, and the regional care pathway data associated with the patient; automatically surfacing the recommendation of the treatment for review by a healthcare personnel within a workflow of the healthcare stewardship program; and administering the treatment to the patient responsive to the review by the healthcare personnel.

According to another innovative aspect of the subject matter described in this disclosure, a system includes: one or more processors; a memory storing instructions, which when executed cause the one or more processors to: receive a plurality of clinical care dataset, historical care dataset, and regional care pathway dataset associated with a plurality of patients in a healthcare stewardship program; train a machine learning model using the plurality of the clinical care dataset, the historical care dataset, and the regional care pathway dataset, the plurality of the clinical care dataset, the historical care dataset, and the regional care pathway dataset including known care events of interest, patient criticality levels, and patient care treatments to train the machine learning model; receive an input of clinical care data, historical care data, and regional care pathway data associated with a patient from the plurality of patients; determine, using the machine learning model, a first output of a patient criticality level, a second output of a care event of interest associated with the patient criticality level, and a third output of a recommendation of a treatment associated with the patient criticality level and the care event of interest based on the input of the clinical care data, the historical care data, and the regional care pathway data associated with the patient; automatically surface the recommendation of the treatment for review by a healthcare personnel within a workflow of the healthcare stewardship program; and administer the treatment to the patient responsive to the review by the healthcare personnel.

These and other implementations may each optionally include one or more of the following operations. For instance, the operations may include: filtering the clinical care data, the historical care data, and the regional care pathway data associated with the patient, generating a clinical dashboard based on the filtering, the first output of the patient criticality level, the second output of the care event of interest, and the third output of the recommendation of the treatment, and presenting the clinical dashboard to the healthcare personnel within the workflow of the healthcare stewardship program; generating an alert notification of the care event of interest, and automatically surfacing, via the clinical dashboard, the alert notification of the care event of interest for review by the healthcare personnel; generating a listing of the plurality of patients in the clinical dashboard, sorting the patient in the listing of the plurality of patients based on the patient criticality level, and associating a graphical indicator with the patient in the listing of the plurality of patients, the graphical indicator indicating a status associated with a review of the patient by the healthcare personnel within the workflow of the healthcare stewardship program; receiving, via the clinical dashboard, a feedback from the healthcare personnel on the first output of the patient criticality level, the second output of the care event of interest, and the third output of the recommendation of the treatment, updating the plurality of the clinical care
dataset, the historical care dataset, and the regional care
pathway dataset based on the feedback, and retraining the
machine learning model using the updated plurality of the
clinical care dataset, the historical care dataset, and the
regional care pathway dataset. Additionally, these and other
implementations may each optionally include one or more of
the following features. For instance, the features may
include the feedback including at least one from a group of
acceptance, rejection, and correction; the clinical dashboard
including healthcare personnel notes, patient vitals trend,
patient medication timeline, patient laboratory results, and
an activity log associated with the treatment of the patient
within the workflow of the healthcare stewardship program;
the patient criticality level being one from a group of low,
medium, and high; the treatment including a therapeutic
procedure, a surgical procedure, a non-surgical procedure, a
laboratory test, a medical test, an imaging test, a medication
prescription, and a follow-up care; the machine learning
model including a neural network assigning a weight to each
of the clinical care data, the historical care data, and the
regional care pathway data associated with the patient; and
the healthcare stewardship program being an antibiotics
stewardship program.

Other implementations of one or more of these aspects
and other aspects include corresponding systems, apparatus,
and computer programs, configured to perform the various
action and/or store various data described in association with
these aspects. Numerous additional features may be
included in these and various other implementations, as
discussed throughout this disclosure.

The features and advantages described herein are not
all-inclusive and many additional features and advantages
will be apparent in view of the figures and description.
Moreover, it should be understood that the language used in
the present disclosure has been principally selected for
readability and instructional purposes, and not to limit the
scope of the subject matter disclosed herein.

BRIEF DESCRIPTION OF THE DRAWINGS

The disclosure is illustrated by way of example, and not
by way of limitation in the figures of the accompanying
drawings in which like reference numerals are used to refer
to similar elements.

FIG. 4 is a block diagram illustrating one implementation
of the care augmentation application in detail.

4

Figure 1:
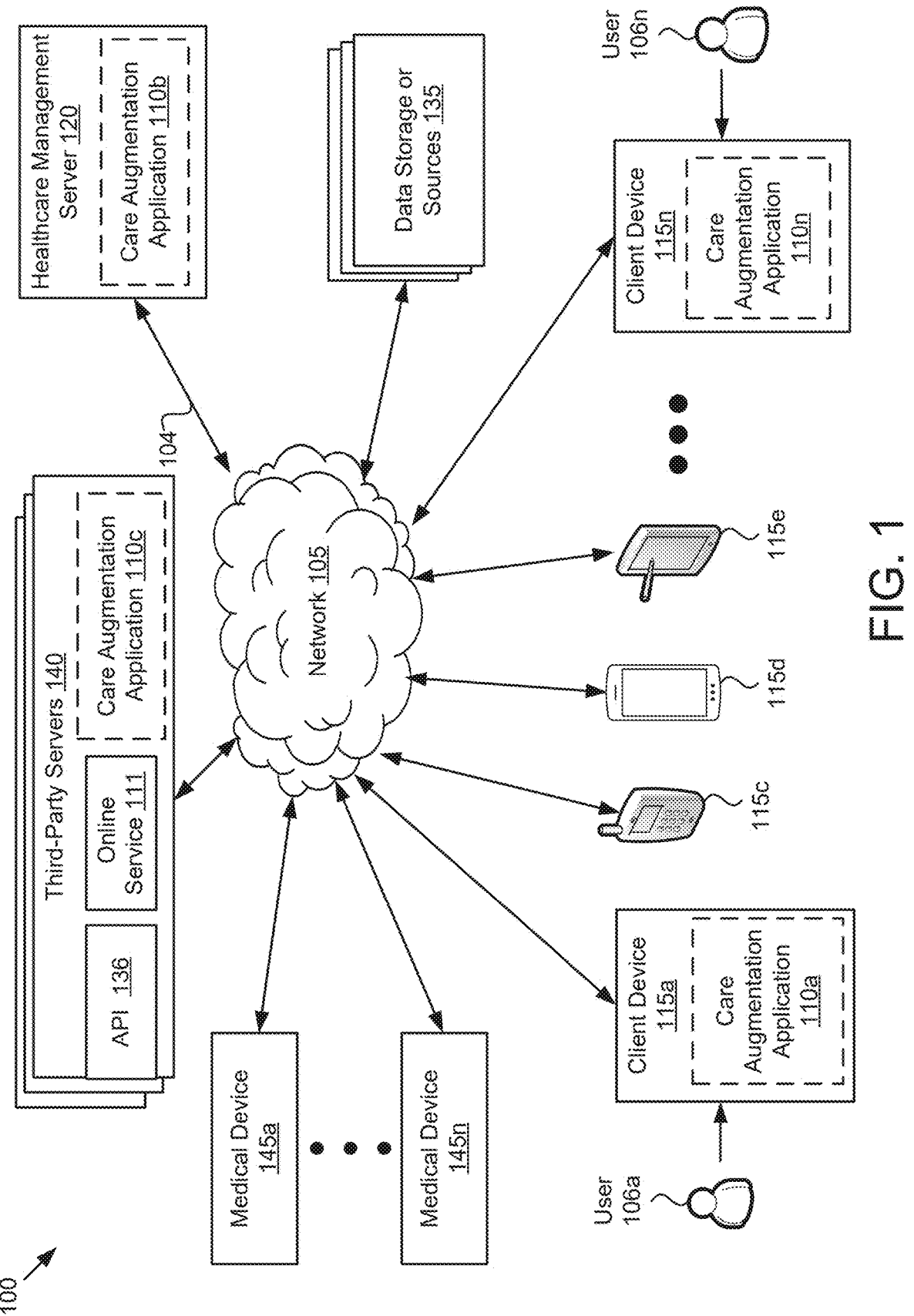
FIG. 1 is a high-level block diagram illustrating one
implementation of an example system for facilitating a
member journey through healthcare service by augmenting
stewardship workflow across multiple service areas.

FIGS. 8-17 show graphical representations of example
user interfaces for a care and clinical dashboard providing
access to care relevant and fact-based intelligence according
to some implementations.

FIG. 18 is a flow diagram illustrating one implementation
of another example method for generating a recommenda-
tion for augmenting a stewardship workflow

DETAILED DESCRIPTION

The techniques introduced herein overcome the deficien-
cies and limitations of the prior art, at least in part, with a
system and methods for augmenting the healthcare steward-
ship workflow by standardizing the healthcare service prac-
tices, increasing the quality of care for patients, improving
the workflow efficiency of healthcare personnel, reducing
the costs associated with providing healthcare services, and
enabling the ease of regulatory compliance using machine
learning techniques. For example, the execution of a health-
care stewardship program at a healthcare facility is a labor
intensive process and can result in a healthcare personnel
working overtime per week per location of the healthcare
facility that is instituting the healthcare practices and care
delivery workflows of the healthcare stewardship program.
In some implementations, the system and methods of the
present disclosure uses artificial intelligence (AI) and
machine learning (ML) based natural language understand-
ing approaches to significantly improve patient experience
and optimize numerous care coordination and care delivery
workflows of the healthcare personnel.

In some implementations, the system and methods of the
present disclosure utilize trained machine learning models to
automatically identify and execute a healthcare stewardship
program at one or more touchpoints of healthcare entity-
patient interactions. A healthcare stewardship program may
be defined as an initiative undertaken by a healthcare related
entity to promote the responsible and efficient management
of healthcare resources while improving patient outcomes
and quality of care. For example, an antimicrobial steward-
ship program is an initiative to combat the potential threat of
antibiotic resistance and such a stewardship program may
begin in less than 24 hours of a patient's admittance to a
hospital based on an indication that the patient has con-
tracted an infection. This ensures that the patient is consis-
tently receiving prompt and timely care in the hospital for
treating the infection and the healthcare personnel are auto-
matically alerted to opportunities to transition the patient
from broad spectrum to narrow spectrum of antibiotics that
is consistent with recommended prescribing practices.

In some implementations, the system and method of the
present disclosure provides the healthcare personnel with
access to healthcare-relevant and fact-based artificial intel-
ligence powered by machine learning for decision support
opportunities to drive recommended care pathways. A care
pathway may be a set of standardized processes for man-
aging a patient's care, typically for a cohort of patients. The
decision support systems optimized by machine learning
based techniques as described herein accelerate the decision
making of the healthcare personnel by decreasing the time
spent by the healthcare personnel on manual processes,
promoting consistency in healthcare delivery workflows and
best practices, and supporting clinically relevant variations
across several healthcare facilities in different geographical
areas.

In some implementations, the system and method of the
present disclosure provides the healthcare personnel with
access to customized user interfaces and/or user experiences for visualizations of healthcare data as described herein. The visualizations of data may be customized using artificial intelligence and machine learning based techniques to increase operational efficiency of the healthcare personnel. In the customized user interfaces and/or user experiences, the patient information residing in disparate data sources are retrieved, processed, and centralized into a single "patient-on-a-page" care and clinical dashboard. For example, one or more operational workflow elements are embedded into the user interface of the care and clinical dashboard and the healthcare personnel may be enabled to tag-and-track critical patients or information allowing them to repurpose their time for other healthcare needs. The data visualization is optimized using machine learning based techniques to process information from disparate sources, such as patient history, patient user profile, medical charts, drugs and dosages, disease indications, physician notes, etc., and surface clinically relevant healthcare data relating to the patients under observation, and facilitate an accelerated review of critical patients by the healthcare personnel via the care and clinical dashboard while meeting compliance, quality, and safety requirements.

In some implementations, the system and method of the present disclosure may use machine learning based techniques for improving healthcare quality and optimizing healthcare outcomes for patients. This approach lowers the gap in care for patients by recommending patient care pathways based upon statistical inferencing. For example, the techniques described herein include analyzing the patient data including current and past biomarkers and their susceptibility to treatment options and recommending a medication for review by the healthcare personnel using one or more trained machine learning models. In another example, the techniques described herein include recommending a timely switch of the medication based upon monitoring a change in the biomarkers of the patient using one or more trained machine learning models. In yet another example, the techniques described herein include automatically balancing user requested notifications and system-generated notifications for a plurality of patients under observation using one or more trained machine learning models such that the health personnel are notified suitably and in a timely manner to attend to the care of patients in a sorted order based on their assessed level of criticalities.

In some implementations, the system and method of the present disclosure may use machine learning based techniques for reducing costs for patients and healthcare related entities providing the healthcare services. This approach reduces the costs by facilitating an adherence to a standard of care, reducing undue variations across geographical areas, enabling timely switch of patient care from one treatment plan to another, enabling remote monitoring of patients where possible, etc. For example, the techniques described herein may recommend a timely switch of expensive and broad spectrum antibiotic medications to targeted antibiotic medications as more patient data is collected and analyzed during the treatment of the patient. In another example, the techniques described herein may decrease physician time to treat a patient and save on overtime costs of the physician. In some implementations, the system and method of the present disclosure may use machine learning based techniques for decreasing cognitive burden of the healthcare personnel. This approach allows the healthcare personnel to efficiently manage their workload by centralizing disparate patient data, providing a holistic view of the patient's care journey, and recommending machine learning-assisted care plans and prescriptions of medications for healthcare personnel's review that reduces treatment time, unnecessary procedures, and laboratory tests. For example, the techniques described herein may allow a cardiologist to manage 750 to 1000 patients that ultimately leads to fewer office visits per patient per year without sacrificing safety, satisfaction, and healthcare outcomes for patients.

The systems and methods of the present disclosure are particularly advantageous because patient satisfaction, care consistency and regulatory compliance are improved while the healthcare costs, the gap in care, and the cognitive burden on healthcare personnel are reduced. For example, the systems and methods of the present disclosure improve regulatory compliance by extending the healthcare stewardship to weekends, ambulatory space, and outpatients. In another example, the systems and methods of the present disclosure improve care consistency by promoting inter and intra-market consistency in healthcare stewardship workflows and best practices. In yet another example, the systems and methods of the present disclosure reduce the gap in care by mitigating antibiotic drug resistance with timely switch from broad to tailored antibiotics. In yet another example, the systems and methods of the present disclosure reduce the healthcare costs by accelerating review of patients under the care of a healthcare personnel with timely notifications of critical care events and recommendations of change in treatment or care plans.

While the present disclosure may describe the techniques herein in the context of an example healthcare stewardship workflow for medical care delivery and coordination in hospitals, medical clinics and the like, it should be understood that the architecture, principles, and components of the present disclosure may also be used to provide automatic attendant services at a front desk, interactive assistance services in an examination room, pharmaceutical prescription and laboratory test ordering systems, email/messaging with primary care provider (PCP) and care team, interaction with chatbots for medical purposes by patients and medical service providers, screening tool for call center agents for medical purposes, on call questions and analytics, medical condition management application/modules, and interactive voice response (IVR) system using voice analytics. The systems and methods described below may be applied to various other medical care, coordination, and delivery procedures in addition to those specifically set forth below.

FIG. 1 is a high-level block diagram illustrating one implementation of an example system 100 for facilitating a member journey through healthcare service by augmenting stewardship workflow across multiple service areas. The illustrated system 100 may include one or more client devices 115a . . . 115n that can be accessed by users, a healthcare management server 120, a plurality of data sources 135, a plurality of third-party servers 140, and a plurality of medical devices 145a . . . 145n which are communicatively coupled via a network 105 for interaction and electronic communication with one another. In FIG. 1 and the remaining figures, a letter after a reference number, e.g., "115a," represents a reference to the element having that particular reference number. A reference number in the text without a following letter, e.g., "115," represents a general reference to instances of the element bearing that reference number The network 105 may be a conventional type, wired or wireless, and may have numerous different configurations including a star configuration, token ring configuration, or other configurations. Furthermore, the network 105 may include any number of networks and/or network types. For example, the network 105 may include a local area network (LAN), a wide area network (WAN) (e.g., the Internet), virtual private networks (VPNs), mobile (cellular) networks, wireless wide area network (WWANs), WiMAX® networks, Bluetooth® communication networks, peer-to-peer networks, near field networks (e.g., NFC, etc.), and/or other interconnected data paths across which multiple devices may communicate, various combinations thereof, etc. The network 105 may also be coupled to or include portions of a telecommunications network for sending data in a variety of different communication protocols. In some implementations, the network 105 may include Bluetooth communication networks or a cellular communications network for sending and receiving data including via short messaging service (SMS), multimedia messaging service (MMS), hypertext transfer protocol (HTTP), direct data connection, WAP, email, etc. In some implementations, the data transmitted by the network 105 may include packetized data (e.g., Internet Protocol (IP) data packets) that is routed to designated computing devices coupled to the network 105. Although FIG. 1 illustrates one network 105 coupled to the client devices 115, the healthcare management server 120, the plurality of data sources 135, the plurality of third-party servers 140, and the medical devices 145, in practice one or more networks 105 can be connected to these entities.

The client devices 115a . . . 115n (also referred to individually and collectively as 115) may be computing devices having data processing and communication capabilities. In some implementations, a client device 115 may include a memory, a processor (e.g., virtual, physical, etc.), a power source, a network interface, software and/or hardware components, such as a display, graphics processing unit (GPU), wireless transceivers, keyboard, camera (e.g., webcam), sensors, firmware, operating systems, web browsers, applications, drivers, and various physical connection interfaces (e.g., USB, HDMI, etc.). The client devices 115a . . . 115n may couple to and communicate with one another and the other entities of the system 100 via the network 105 using a wireless and/or wired connection. Examples of client devices 115 may include, but are not limited to, laptops, desktops, tablets, mobile phones (e.g., smartphones, feature phones, etc.), server appliances, servers, virtual machines, smart TVs, media streaming devices, user wearable computing devices (e.g., fitness trackers, etc.) or any other electronic device capable of accessing a network 105. In the example of FIG. 1, the client device 115a is configured to implement a care augmentation application 110a described in more detail below. The client device 115 includes a display for viewing information provided by one or more entities coupled to the network 105. For example, the client device 115 may be adapted to send and receive data to and from the healthcare management server 120. While two or more client devices 115 are depicted in FIG. 1, the system 100 may include any number of client devices 115. In addition, the client devices 115a . . . 115n may be the same or different types of computing devices. The client devices 115a . . . 115n may be associated with members of a healthcare organization, such as the users 106a . . . 106n. For example, users 106a . . . 106n may include patient members, physicians, clinical staff, laboratory technicians, pharmacy technicians, administrative staff, call center agents, subject matter experts, etc. of a health care organization. Each client device 115 may be associated with a data channel, such as a mobile application running on a user's smartphone, a computer in a doctor's office, a health tracking device, etc. These data channels may collect data related to one or more users and provide that data to the entities coupled to the network 105. In some implementations, the client devices 115 may be implemented as a computing device 200 as will be described below with reference to FIG. 2.

The medical devices 145a . . . 145n may include, but are not limited to, a stethoscope, a blood pressure meter, a pulse oximeter, a thermometer, an ophthalmoscope, a weight and height scale, an otoscope, a camera, a telecardiology device (e.g. an ECG machine), a telepathology device (e.g. a microscope), a teledermatology device (e.g. a high-resolution camera), a teleradiology device (e.g. an ultrasound machine), a medical radiography equipment (e.g., MRI machine, CT machine, X-ray machine, etc.), etc. associated with one or more health care organizations. Authorized personnel who are trained to use the medical device 145 may obtain the patient's medical information. For example, the authorized personnel may include physicians and clinical staff. In some implementations, the medical device 145 may cooperate with the client device 115 to allow authorized personnel to communicate with other entities of the system 100. For example, the client device 115 receives a report associated with a patient including a medical test result from the medical device 145, and sends the report to the healthcare management server 120 for storage and analysis.

In the example of FIG. 1, each one of the healthcare management server 120, the plurality of data sources 135, the plurality of medical devices 145, and the plurality of the third-party servers 140 may be, or may be implemented by, a computing device including a processor, a memory, applications, a database, and network communication capabilities similar to that described below with reference to FIG. 2.

In the example of FIG. 1, the healthcare management server 120 may be configured to implement a care augmentation application 110b. In some implementations, the healthcare management server 120 may be a hardware server, a software server, or a combination of software and hardware. For example, the healthcare management server 120 may include one or more hardware servers, virtual servers, server arrays, storage devices and/or systems, etc., and/or may be centralized or distributed/cloud-based. In some implementations, the healthcare management server 120 may include one or more virtual servers, which operate in a host server environment and access the physical hardware of the host server including, for example, a processor, a memory, applications, a database, storage, network interfaces, etc., via an abstraction layer (e.g., a virtual machine manager). In some implementations, the healthcare management server 120 may be a Hypertext Transfer Protocol (HTTP) server, a Representational State Transfer (REST) service, or other server type, having structure and/or functionality for processing and satisfying content requests and/ or receiving content from one or more of the client devices 115, one or more of the medical devices 145, the plurality of data sources 135, and the plurality of third-party servers 140 that are coupled to the network 105.

Also, instead of or in addition, the healthcare management server 120 may implement its own application programming interface (API) for the transmission of instructions, data, results, and other information between the server 120 and other entities communicatively coupled to the network 105. For example, the API may be a software interface exposed over the HTTP protocol by the healthcare management server 120. The API exposes internal data and functionality of the service hosted by the healthcare management server 120 to API requests originating from one or more of the care augmentation application 110, the plurality of data sources 135, and the plurality of third-party servers 140. In one example, the care augmentation application 110b implemented by the healthcare management server 120 passes an authenticated request including a set of parameters for information to one or more of the third-party server 140 and the data source 135 and receives an object (e.g., XML or JSON) with associated results. In some implementations, the healthcare management server 120 may also include a database coupled to it (e.g., over the network 105) to store structured data in a relational database and a file system (e.g., HDFS, NFS, etc.) for unstructured or semi-structured data. In some implementations, the healthcare management server 120 may include an instance of a data store that stores various types of data for access and/or retrieval by the care augmentation application 110. For example, the data store may store machine learning models for disease indication identification, criticality determination, care pathway and medication prescription recommendation. Other types of user data are also possible and contemplated.

In some implementations, the healthcare management server 120 sends and receives data to and from other entities of the system 100 via the network 105. For example, the healthcare management server 120 sends and receives data including instructions to and from the client device 115. In some implementations, the healthcare management server 120 may serve as a middle layer and permit interactions between the client device 115 and the plurality of medical devices 145, the plurality of the third-party servers 140 and the data sources 135 to flow through and from the healthcare management server 120 for security and convenience. In some implementations, the healthcare management server 120 may be operable to receive a stream of raw patient data from disparate data sources, process, filter and store them accordingly, assess criticality of a patient, surface an alert notification for care events of interest, and automatically recommend a care pathway for treating the patient to a healthcare provider to review and authorize for administration based on one or more trained machine learning models, etc. The healthcare management server 120 may send data to and receive data from the other entities of the system 100 via the network 105. It should be understood that the healthcare management server 120 is not limited to providing the above-noted acts and/or functionality and may include other network-accessible services. In addition, while a single healthcare management server 120 is depicted in FIG. 1, it should be understood that there may be any number of healthcare management servers 120 or a server cluster. Each one of the healthcare management servers 120 may be associated with a healthcare facility at different geographical locations providing a stewardship of care as described herein.

Each of the one or more third-party servers 140 may be, or may be implemented by, a computing device including a processor, a memory, applications, a database, and network communication capabilities. A third-party server 140 may be a Hypertext Transfer Protocol (HTTP) server, a Representational State Transfer (REST) service, or other server type, having structure and/or functionality for processing and satisfying content requests and/or requesting and receiving content from one or more of the client devices 115, the medical devices 145, the data sources 135, and the healthcare management server 120 that are coupled to the network 105. In some implementations, the third-party server 140 may include an online service 111 dedicated to providing access to various services and information resources hosted by the third-party server 140 via web, mobile, enterprise, and/or cloud applications. The online service 111 may obtain and store user data, user-generated data, content items (e.g., videos, text, images, etc.), and interaction data reflecting the interaction of users with the content items. In some implementations, the third-party server 140 may provide an API 136 to facilitate access of the third-party server 140 by one or more of the client devices 115, the medical devices 145, the data sources 135, and the healthcare management server 120 that are coupled to the network 105. User-generated data, as described herein, may include one or more of user profile information (e.g., user id, user preferences, user history, social network connections, primary care physicians, etc.), logged information (e.g., heart rate, activity metrics, sleep quality data, calories and nutrient data, user device specific information, historical actions, medication history, etc.), and other user specific information. In some implementations, the online service 111 allows users to share content with other users (e.g., friends, contacts, public, similar users, primary care physicians, clinical staff, administrative staff, etc.), purchase and/or view items (e.g., e-books, videos, music, games, subscription, fitness products, prescription refill, laboratory results, etc.), and other similar actions. For example, the online service 111 may provide various services such as digital fitness content; personal training; running and cycling tracking service; music streaming service; mobile health (mHealth) service; video streaming service; web mapping service; multimedia messaging service; electronic mail service; a calendar service; news service; news aggregator service; social networking service; location-based service; photo and video-sharing social networking service; sleep-tracking service; diet-tracking and calorie counting service; ridesharing service; online banking service; online information database service; travel service; online e-commerce marketplace; ratings and review service; restaurant-reservation service; food delivery service; search service; health and fitness service; home automation and security service; Internet of Things (IoT), multimedia hosting, distribution, and sharing service; cloud-based data storage and sharing service; a scheduling service; an enterprise clinical workflow service; a combination of one or more of the foregoing services; or any other service where users retrieve, collaborate, and/or share information, etc. It should be noted that the list of items provided above as examples for the online service 111 above are not exhaustive and that others are contemplated in the techniques described herein.

Each of the plurality of data sources 135 may be, or may be implemented by, a computing device including a processor, a memory, applications, a database, and network communication capabilities. In some implementations, the data sources may be a data warehouse, a system of record (SOR), or belonging to a data repository owned by an organization that provides real-time or close to real-time data automatically or responsive to being polled or queried by the healthcare management server 120. Each of the plurality of data sources 135 may be associated with a first-party entity (e.g., server 120) or third-party entity (e.g., server 140 associated with a separate company or service provider), such as a health insurance organization, a health care organization, a governmental organization, world health organization, an independent healthcare provider, a healthcare-related call center or customer service company, a healthcare software company, an Electronic Medical Record (EMR) software company, an Electronic Health Record (EHR) software company, a pharmacy management system, a drug research institute, a patient management software system, a clinical decision support system, a clinical workflow management system, a scheduling system, a patient-satisfaction measurement firm, a medication adherence tracking system, a public-records database, a data mining platform, a Software as a Service (SaaS) data analytics company, a data science and machine learning platform, news site, support groups, health blogs, etc. Examples of data provided by the plurality of data sources 135 may include, but is not limited to, pharmacy data, physician-patient encounter data, clinical data, patient data, EMR, EHR, patient diagnosis data, patient procedures, appointment notes, socioeconomic data, social determinant data, demographic data, health plan data, prescription data, call center data, appointment schedule data, disposition data, calendar data, medication data, pharmaceutical data, survey data, medication adherence data, machine learning models, machine learning-based data analysis results, etc. In some implementations, each of the plurality of data sources 135 may be configured to provide or facilitate an API (not shown) that allows the care augmentation application 110 to access data and information for performing the functionality described herein.

The care augmentation application 110 may include software and/or logic to provide the functionality for facilitating and augmenting a healthcare service stewardship workflow across multiple service areas. In some implementations, the care augmentation application 110 may be implemented using programmable or specialized hardware, such as a field-programmable gate array (FPGA) or an application-specific integrated circuit (ASIC). In some implementations, the care augmentation application 110 may be implemented using a combination of hardware and software. In one implementation, the care augmentation application 110b is stored and executed on healthcare management server 120 alone. In another implementation, the care augmentation application 110a, 110n is stored and executed on client device 115 alone. In other implementations, the care augmentation application 110 may be stored and executed on various combinations of the medical devices 145, the client device 115, the data sources 135, the third-party servers 140, and the healthcare management server 120, or by any one of the medical devices 145, the client devices 115, the data sources 135, the third-party servers 140, or the healthcare management server 120.

In some implementations, the care augmentation application 110a may be a thin-client application with some functionality executed on the client device 115 and additional functionality executed on the healthcare management server 120 by the care augmentation application 110b. In some implementations, the care augmentation application 110 may generate and present various user interfaces to perform these acts and/or functionality, which may in some cases be based at least in part on information received from the healthcare management server 120, the client device 115, the medical device 145, one or more of the third-party servers 140 and/or the data sources 135 via the network 105. Non-limiting example user interfaces that may be generated for display by the care augmentation application 110 include FIGS. 8-17. In some implementations, the care augmentation application 110 is code operable in a web browser, a web application accessible via a web browser, a native application (e.g., mobile application, installed application, etc.) on the client device 115, the servers 120, 140, a combination thereof, etc. Additional structure, acts, and/or functionality of the care augmentation application 110 is further discussed below with reference to at least FIG. 2.

In some implementations, the care augmentation application 110 may require users to be registered with the healthcare management server 120 to access the acts and/or functionality described herein. For example, to access various acts and/or functionality provided by the care augmentation application 110, the care augmentation application 110 may require a user to authenticate his/her identity. For example, the care augmentation application 110 may require a user seeking access to authenticate their identity by inputting credentials in an associated user interface. In another example, the care augmentation application 110 may interact with a federated identity server (not shown) to register and/or authenticate the user by scanning and verifying biometrics including username and password, facial attributes, fingerprint, and voice.

Other variations and/or combinations are also possible and contemplated. It should be understood that the system 100 illustrated in FIG. 1 is representative of an example system and that a variety of different system environments and configurations are contemplated and are within the scope of the present disclosure. For example, various acts and/or functionality may be moved from a server 120 to a client device 115, or vice versa, data may be consolidated into a single data store or further segmented into additional data stores, and some implementations may include additional or fewer computing devices, services, and/or networks, and may implement various functionality client or server-side. Furthermore, various entities of the system may be integrated into a single computing device or system or divided into additional computing devices or systems, etc.

Figure 2:
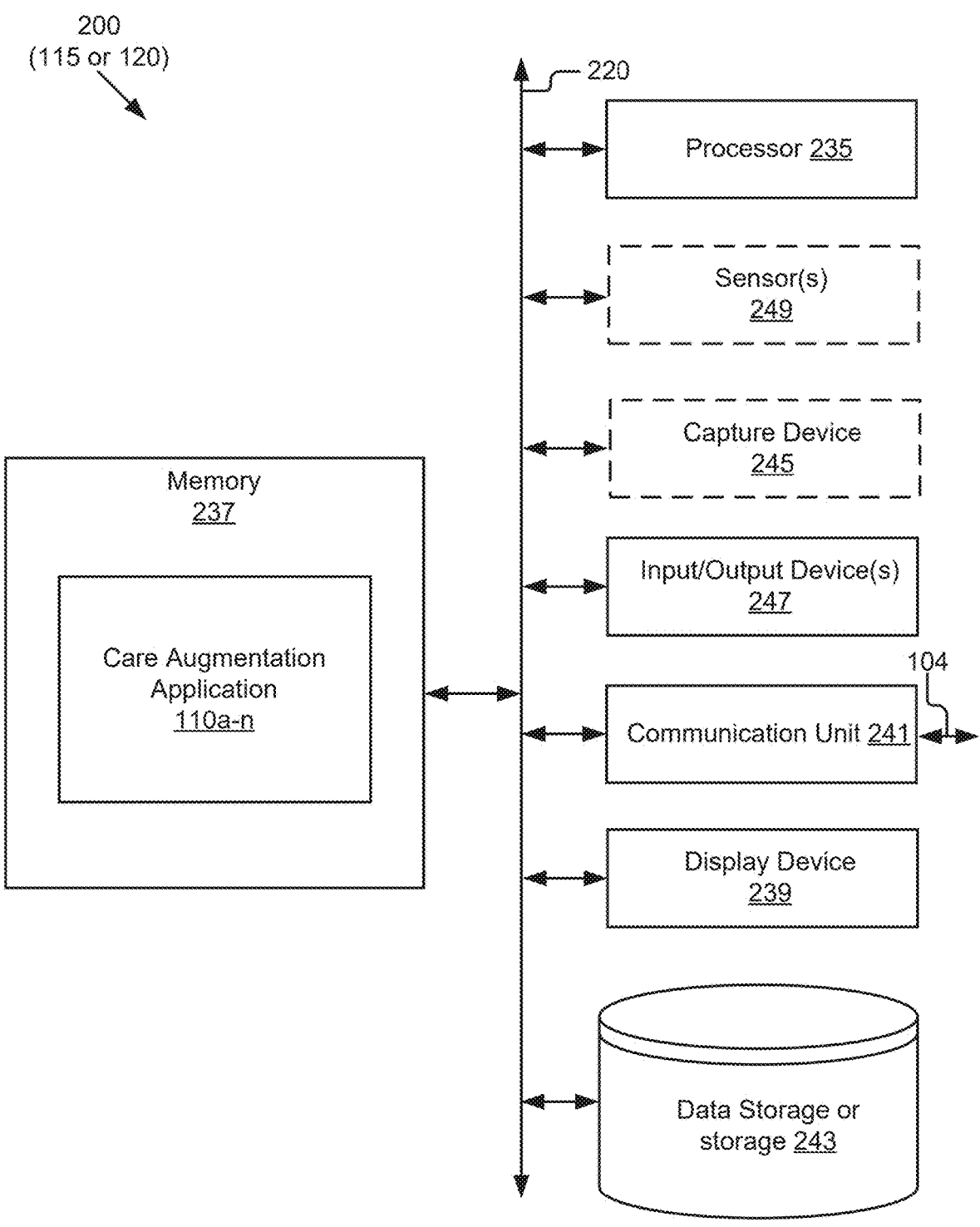
FIG. 2 is a block diagram illustrating one implementation
of a computing device including a care augmentation appli-
cation.

FIG. 2 is a block diagram illustrating one implementation of a computing device 200 including a care augmentation application 110. The computing device 200 may also include a processor 235, a memory 237, a display device 239, a communication unit 241, a capture device 245, one or more sensor(s) 249, an input/output device(s) 247, and a data storage 243, according to some examples. The components of the computing device 200 are communicatively coupled by a bus 220. In some implementations, the computing device 200 may be representative of the client device 115, the healthcare management server 120, or a combination of the client device 115 and the healthcare management server 120. In such implementations where the computing device 200 is the client device 115 or the healthcare management server 120, it should be understood that the client device 115 and the healthcare management server 120 may take other forms and include additional or fewer components without departing from the scope of the present disclosure. For example, while not shown, the computing device 200 may include sensors 249, capture devices 245, additional processors, and other physical configurations. Additionally, it should be understood that the computer architecture depicted in FIG. 2 could be applied to other entities of the system 100 with various modifications, including, for example, the servers 140 and data sources 135.

The processor 235 may execute software instructions by performing various input/output, logical, and/or mathematical operations. The processor 235 may have various computing architectures to process data signals including, for example, a complex instruction set computer (CISC) architecture, a reduced instruction set computer (RISC) architecture, and/or an architecture implementing a combination of instruction sets. The processor 235 may be physical and/or virtual, and may include a single processing unit or a plurality of processing units and/or cores. In some implementations, the processor 235 may be capable of generating and providing electronic display signals to a display device 239, supporting the display of images, capturing and transmitting images, and performing complex tasks including various types of feature extraction and sampling. In some implementations, the processor 235 may be coupled to the memory 237 via the bus 220 to access data and instructions therefrom and store data therein. The bus 220 may couple the processor 235 to the other components of the computing device 200 including, for example, the memory 237, the communication unit 241, the display device 239, the input/output device(s) 247, and the data storage 243.

The memory 237 may store and provide access to data for the other components of the computing device 200. The memory 237 may be included in a single computing device or distributed among a plurality of computing devices as discussed elsewhere herein. In some implementations, the memory 237 may store instructions and/or data that may be executed by the processor 235. The instructions and/or data may include code for performing the techniques described herein. For example, as depicted in FIG. 2, the memory 237 may store the care augmentation application 110. The memory 237 is also capable of storing other instructions and data, including, for example, an operating system, hardware drivers, other software applications, databases, etc. The memory 237 may be coupled to the bus 220 for communication with the processor 235 and the other components of the computing device 200.

The memory 237 may include one or more non-transitory computer-usable (e.g., readable, writeable) device, a static random access memory (SRAM) device, a dynamic random access memory (DRAM) device, an embedded memory device, a discrete memory device (e.g., a PROM, FPROM, ROM), a hard disk drive, an optical disk drive (CD, DVD, Blu-ray™, etc.) mediums, which can be any tangible apparatus or device that can contain, store, communicate, or transport instructions, data, computer programs, software, code, routines, etc., for processing by or in connection with the processor 235. In some implementations, the memory 237 may include one or more of volatile memory and non-volatile memory. It should be understood that the memory 237 may be a single device or may include multiple types of devices and configurations.

The bus 220 may represent one or more buses including an industry standard architecture (ISA) bus, a peripheral component interconnect (PCI) bus, a universal serial bus (USB), or some other bus providing similar functionality. The bus 220 may include a communication bus for transferring data between components of the computing device 200 or between computing device 200 and other components of the system 100 via the network 105 or portions thereof, a processor mesh, a combination thereof, etc. In some implementations, the care augmentation application 110 and various other software operating on the computing device 200 (e.g., an operating system, device drivers, etc.) may cooperate and communicate via a software communication mechanism implemented in association with the bus 220. The software communication mechanism may include and/or facilitate, for example, inter-process communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication may be configured to be secure (e.g., SSH, HTTPS, etc.).

The display device 239 may be any conventional display device, monitor or screen, including but not limited to, a liquid crystal display (LCD), light emitting diode (LED), organic light-emitting diode (OLED) display or any other similarly equipped display device, screen or monitor. The display device 239 represents any device equipped to display user interfaces, electronic images, and data as described herein. In some implementations, the display device 239 may output display in binary (only two different values for pixels), monochrome (multiple shades of one color), or multiple colors and shades. The display device 239 is coupled to the bus 220 for communication with the processor 235 and the other components of the computing device 200. In some implementations, the display device 239 may be a touch-screen display device capable of receiving input from one or more fingers of a user. For example, the display device 239 may be a capacitive touch-screen display device capable of detecting and interpreting multiple points of contact with the display surface. In some implementations, the computing device 200 (e.g., client device 115) may include a graphics adapter (not shown) for rendering and outputting the images and data for presentation on display device 239. The graphics adapter (not shown) may be a separate processing device including a separate processor and memory (not shown) or may be integrated with the processor 235 and memory 237.

The input/output (I/O) device(s) 247 may include any standard device for inputting or outputting information and may be coupled to the computing device 200 either directly or through intervening I/O controllers. In some implementations, the input device 247 may include one or more peripheral devices. Non-limiting example I/O devices 247 include a touch screen or any other similarly equipped display device equipped to display user interfaces, electronic images, and data as described herein, a touchpad, a keyboard, a scanner, a stylus, an audio reproduction device (e.g., speaker), a microphone array, a barcode reader, an eye gaze tracker, a sip-and-puff device, and any other I/O components for facilitating communication and/or interaction with users. In some implementations, the functionality of the input/output device 247 and the display device 239 may be integrated, and a user of the computing device 200 (e.g., client device 115) may interact with the computing device 200 by contacting a surface of the display device 239 using one or more fingers. For example, the user may interact with an emulated (i.e., virtual or soft) keyboard displayed on the touch-screen display device 239 by using fingers to contact the display in the keyboard regions.

The communication unit 241 is hardware for receiving and transmitting data by linking the processor 235 to the network 105 and other processing systems via signal line 104. The communication unit 241 receives data such as requests from the client device 115 and transmits the requests to the care augmentation application 110, for example a request to schedule an appointment with a health care provider. The communication unit 241 also transmits information including media to the client device 115 for display, for example, in response to the request. The communication unit 241 is coupled to the bus 220. In some implementations, the communication unit 241 may include a port for direct physical connection to the client device 115 or to another communication channel. For example, the communication unit 241 may include an RJ45 port or similar port for wired communication with the client device 115. In other implementations, the communication unit 241 may include a wireless transceiver (not shown) for exchanging data with the client device 115 or any other communication channel using one or more wireless communication methods, such as IEEE 802.11, IEEE 802.16, Bluetooth® or another suitable wireless communication method.

In yet other implementations, the communication unit 241 may include a cellular communications transceiver for sending and receiving data over a cellular communications network such as via short messaging service (SMS), multimedia messaging service (MMS), hypertext transfer protocol (HTTP), direct data connection, WAP, e-mail or another suitable type of electronic communication. In still other implementations, the communication unit 241 may include a wired port and a wireless transceiver. The communication unit 241 also provides other conventional connections to the network 105 for distribution of files and/or media objects using standard network protocols such as TCP/IP, HTTP, HTTPS, and SMTP as will be understood to those skilled in the art.

The data storage 243 is a non-transitory memory that stores data for providing the functionality described herein. In some implementations, the data storage 243 may be coupled to the components 235, 237, 239, 241, 243, 245, 247 and 249 via the bus 220 to receive and provide access to data. In some implementations, the data storage 243 may store data received from other elements of the system 100 including, for example, entities 135, 140, 145, and/or the care augmentation application s 110, and may provide data access to these entities.

Figure 3:
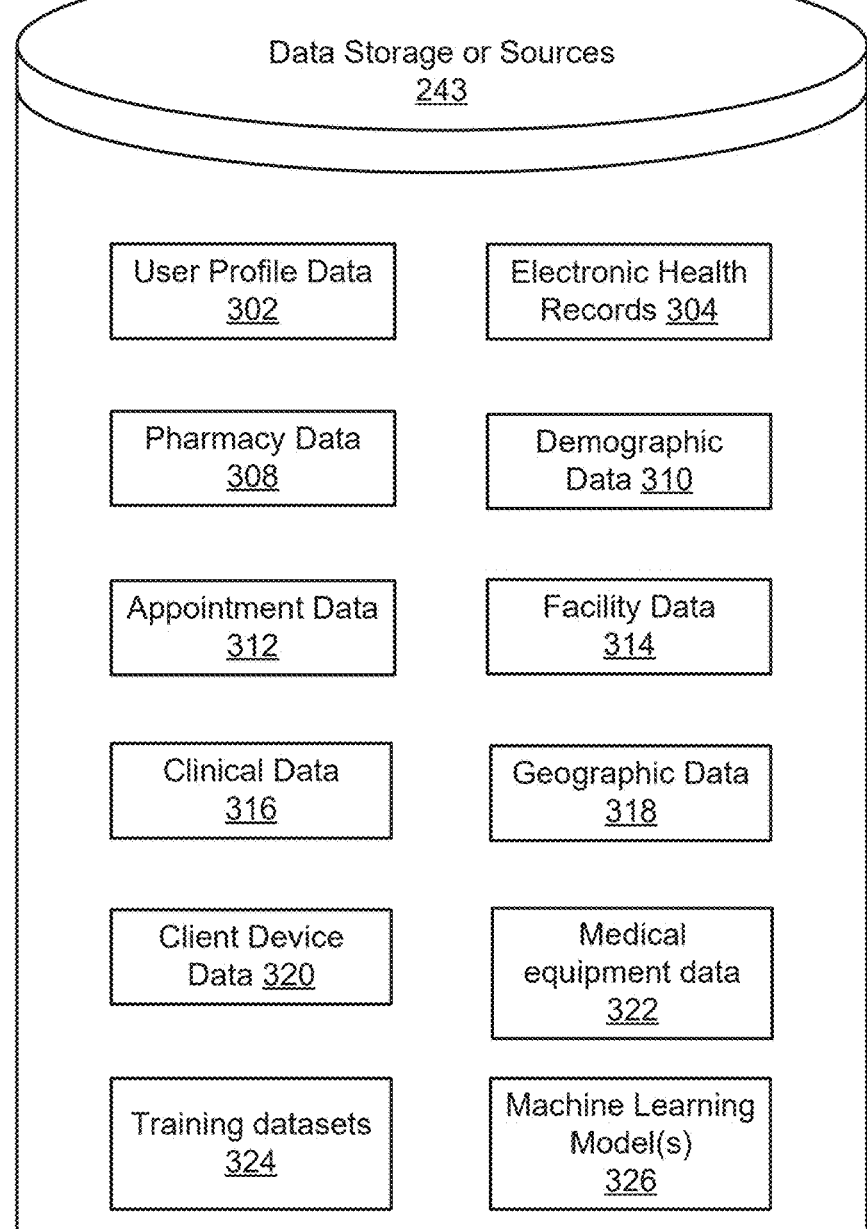
FIG. 3 is a block diagram illustrating one implementation
of the data storage of the computing device in FIG. 2 in
detail.

FIG. 3 is a block diagram illustrating one implementation of the data storage of the computing device in FIG. 2 in detail. The data storage 243 may store, among other data, user profile data 302, electronic medical records/electronic health records (EMR/EHR) 304, pharmacy data 308, demographic data 310, appointment data 312, facility data 314, clinical data 316, geographic data 318, client device data 320, medical equipment data 322, training datasets 324, machine learning models 326, application metadata 328, transaction data 330, enterprise clinical and member workflow data 332, other data 334, etc., In some implementations, the workflow data 332 may not be stored separately in the data storage 243 but instead be stored as part of the metadata 328. The data storage 243 stores data associated with facilitating and augmenting healthcare service stewardship workflow across multiple service areas and other functionality as described herein. The data stored in the data storage 243 is described below in more detail.

The data storage 243 may be included in the computing device 200 or in another computing device and/or storage system distinct from but coupled to or accessible by the computing device 200. The data storage 243 may include one or more non-transitory computer-readable mediums for storing the data. In some implementations, the data storage 243 may be incorporated with the memory 237 or may be distinct therefrom. The data storage 243 may be a dynamic random-access memory (DRAM) device, a static random-access memory (SRAM) device, flash memory, or some other memory devices. In some implementations, the data storage 243 may include a database management system (DBMS) operable on the computing device 200. For example, the DBMS could include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations. In other implementations, the data storage 243 also may include a non-volatile memory or similar permanent storage device and media including a hard disk drive, a CD-ROM device, a DVD-ROM device, a DVD-RAM device, a DVD-RW device, a flash memory device, or some other mass storage device for storing information on a more permanent basis.

It should be understood that other processors, operating systems, sensors, displays, and physical configurations are possible.

As depicted in FIG. 2, the memory 237 may include the care augmentation application 110. In some implementations, the care augmentation application 110 may be configured to implement a secure HTTP API (not shown) to facilitate web, mobile, enterprise, and/or cloud applications to facilitate healthcare service stewardship across multiple service areas.

As depicted in FIG. 4, in some implementations, the care augmentation application 110 may include a patient journey engine 402, a clinician journey engine 404, and a care pathway recommendation engine 406. The components 402, 404, and 406 may be communicatively coupled by the bus 220 and/or the processor 235 to one another and/or the other components 237, 239, 241, 243, 245, 247, and 249 of the computing device 200 for cooperation and communication. The components 402, 404, and 406 may each include software and/or logic to provide their respective functionality. In some implementations, the components 402, 404, and 406 may each be implemented using programmable or specialized hardware including a field-programmable gate array (FPGA) or an application-specific integrated circuit (ASIC). In some implementations, the components 402, 404, and 406 may each be implemented using a combination of hardware and software executable by the processor 235. In some implementations, each one of the components 402, 404, and 406 may be sets of instructions stored in the memory 237 and configured to be accessible and executable by the processor 235 to provide their acts and/or functionality. In some implementations, the components 402, 404, and 406 may send and receive data, via the communication unit 241, to and from one or more of the client devices 115, the medical devices 145, the healthcare management server 120, the data sources 135, and third-party servers 140.

A patient journey engine 402 may include software and/or logic to provide functionality for facilitating a patient member journey through healthcare services by providing one or more non-physician practitioners with access to care relevant and fact-based intelligence that accelerates their decision making at one or more touchpoints of the patient member journey. For example, a touchpoint of the patient member journey may include any healthcare entity-patient interaction. In another example, the non-physician practitioner may include but is not limited to a nurse practitioner, a physician assistant, a pharmacist, a social worker, a dental hygienist, etc. In some implementations, the patient journey engine 402 may facilitate the non-physician practitioner with providing a stewardship of care to the patient members in association with a diagnosis of a health condition, a comorbidity, a disease, a prescription of a medication, a prescription of a laboratory test, a review of vitals, biomarkers, allergies, drug-bug mismatch, drug interaction, etc. For example, the patient journey engine 402 may facilitate a stewardship for managing a prescription of a drug to treat obesity, opioid addiction, heart disease, kidney disease, cancer, arthritis, diabetes, etc. In another example, the stewardship for managing the prescription of the drug may include managing the reduction of costs associated with the prescription drug, the determination of eligibility to receive the prescription drug, the determination of a route of delivery for administering the prescription drug, the determination of a replacement drug, etc.

In some implementations, the patient journey engine 402 tracks a patient and their corresponding data including clinical encounter data and historical care data when the patient is scheduled for a visit or admitted at the healthcare entity for receiving a healthcare service. For example, if a patient is diagnosed with an infection by an attending physician, the patient journey engine 402 tracks one or more touchpoints including but not limited to the admittance of the patient (e.g., number of days that the patient is staying, number of days since the start of the infection in the patient, day of discharge, etc.), the collection of samples (e.g., blood, urine, stool, sputum, etc.) as per the laboratory tests prescribed by the attending physician, the aggregation of test results, medications ordered, medications administered, route of medication delivery (e.g., oral, intravenous, patch, intramuscular, subcutaneous, rectal, inhalation, intraperitoneal, intradermal, topical, ocular, transdermal, etc.), etc. In another example, the patient journey engine 302 extracts the corresponding patient data from the electronic health records 404, the pharmacy data 408, appointment data 312, facility data 314, transaction data 330, etc. The patient journey engine 402 uses one or more trained machine learning models 322 to process the data associated with the one or more touchpoints of the patient member journey for the visit and generate a care recommendation that optimizes the patient member journey for the consideration of the non-physician practitioner. In some implementations, the patient journey engine 402 may optimize the patient journey along the lines of consistency of care (e.g. increase consistency of care), regulatory compliance (e.g., increase regulatory compliance), costs (e.g., decrease costs), gap in care (e.g., decrease the gap in care), cognitive burden (e.g., decrease cognitive burden) of the non-physician practitioner, etc. For example, the patient journey engine 402 may generate a care recommendation that suggest a change in medication (e.g., broad spectrum to narrow spectrum of antibiotics) for the non-physician practitioner to review and push to the physician practitioner for approval. In another example, the patient journey engine 402 may track a criticality level of a patient and notify the non-physician practitioner in real-time or close to real-time about the release of published results of a laboratory test ordered for the patient. The patient journey engine 402 reduces the care gap by extending the stewardship of care provided to patient members from weekdays to weekends. For example, the patient journey engine 402 may facilitate switching a patient member who was started on a broad spectrum antibiotics regimen on Thursday to a narrow spectrum antibiotics sooner on the weekend (if patient member's vitals or biomarkers necessitate such a change) rather than delaying it to the following Monday. This reduction of care gap saves healthcare costs because the usage of expensive broad spectrum antibiotics is reduced.

A clinician journey engine 404 may include software and/or logic to provide functionality for facilitating a clinician member journey through healthcare services by providing the clinician member with access to care relevant and fact-based intelligence that accelerates their decision making at one or more touchpoints of the clinician member journey. For example, a touchpoint of the clinician member journey may include any clinician member-patient member interaction. In another example, the clinician member may include a practitioner, such as a physician, dentist, surgeon, cardiologist, infectious disease specialist, nephrologist, oncologist, ophthalmologist, etc. Similar to the optimization described for the patient journey, the clinician journey engine 404 tracks patient member data including clinical encounter data and historical care data of the patient member and their cohorts. The clinician journey engine 404 uses one or more trained machine learning models 322 to process the data associated with the patient member and generate a recommendation that optimizes the clinician journey. In some implementations, the clinician journey engine 404 may optimize the clinician journey along the lines of consistency of care (e.g. increase consistency of care), regulatory compliance (e.g., increase regulatory compliance), costs (e.g., decrease costs), gap in care (e.g., decrease the gap in care), cognitive burden (e.g., decrease cognitive burden) of the physician practitioner, etc. For example, if a patient is presenting at the hospital for receiving healthcare service, the clinician journey engine 404 may use a natural language processing (NLP) and/or natural language understanding (NLU) model to process the physician notes taken at a specific patient-physician encounter and identify and extract the primary, secondary, and/or tertiary indications of the patient. In another example, the clinician journey engine 404 may recommend a laboratory test for the physician to review and order on behalf of the patient member based on the current indications and historical data of the patient member and their cohorts. In yet another example, the clinician journey engine 404 may recommend a drug to treat the primary indication of the patient member for the physician to review and prescribe for the patient member.

A care pathway recommendation engine 406 may include software and/or logic to provide functionality for facilitating a healthcare organization to operate at the top of its licensure by providing machine learning-assisted decision support to drive recommended care pathways. Similar to the optimization described for the patient journey and clinician journey above, the care pathway recommendation engine 406 tracks regional care pathway data of the patient member and their cohorts. The care pathway recommendation engine 406 uses one or more trained machine learning models 322 to process the regional care pathway data associated with the patient member and their cohorts to generate a recommendation that optimizes the care pathway. In some implementations, the care pathway recommendation engine 406 may increase the operational efficiency of the healthcare organization. One problem is there is no consistent way of executing a stewardship of care across multiple geographies, medical centers, regions, or sub-regions. For example, each medical center may use their own tailored or standardized version of a solution that relies on different tools, drugs, treatment plans, etc. The care pathway recommendation engine 406 improves care outcomes of the patient members irrespective of their geographical location by reducing variations in care plans while honoring the clinically relevant variations in care plans across different geographical locations. The care pathway recommendation engine 406 may recommend an alternative treatment plan for a patient if the patient data matches the alternative treatment plan (that is favored at another hospital in a different geographical location) as opposed to a preferred treatment plan followed in the hospital where the patient is currently visiting. For example, if a patient member complained of chest pain but the results of a clinical test ordered for the patient member returns the presence of asymptomatic symptoms, the care pathway recommendation engine 406 may recommend an alternative care pathway where a nurse practitioner attends to the patient member instead of a routine care pathway where an appointment is scheduled with a cardiologist at the hospital. In some implementations, the care pathway recommendation engine 406 may reduce the cost of healthcare services. For example, the care pathway recommendation engine 406 may surface alerts to pharmacists to timely transition patients to a different medication based on a change in biomarkers (e.g., neutrophils, metamyelocytes, etc.) found in test results of the patient. This results in a targeted treatment plan that lowers costs to the organization. In another example, the care pathway recommendation engine 406 lowers costs through treatment recommendations that decrease physician overtime without sacrificing quality of care.

Figure 5:
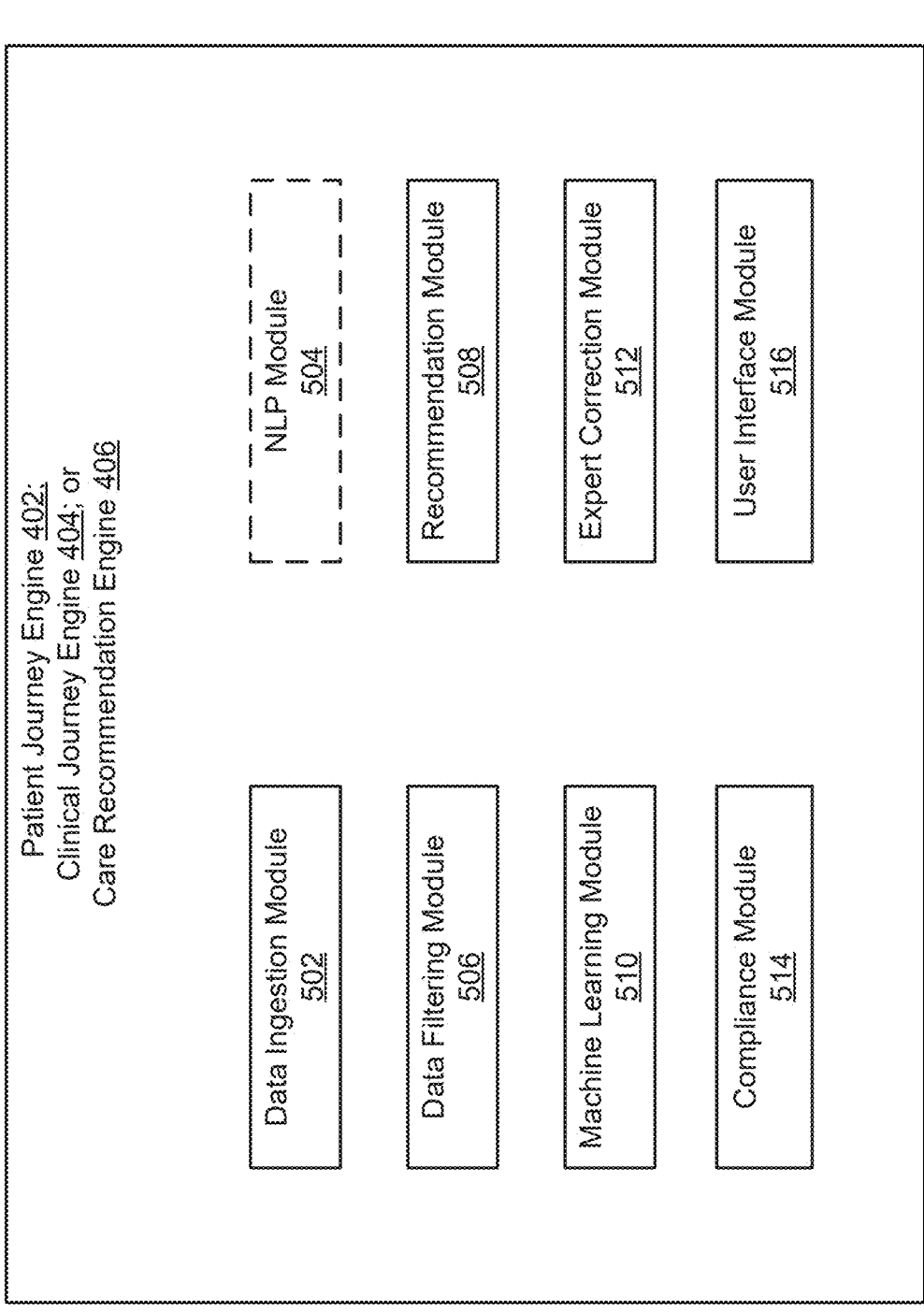
FIG. 5 is a block diagram illustrating one implementation
of the patient journey engine, clinician journey engine, or
care recommendation engine in detail.

As depicted in FIG. 5, each one of the components patient journey engine 302, clinician journey engine 304, and care recommendation engine 306 may include a data ingestion module 502, a natural language processing (NLP) module 504, a data filtering module 506, a recommendation module 508, a machine learning module 510, an expert correction module 512, and a user interface module 514.

The data ingestion module 502 may include software and/or logic to provide functionality for receiving, processing, and storing a stream of data received from one or more entities of the system 100. The stream of data may correspond to a plurality of users in a healthcare stewardship workflow, such as patient members, physicians, clinical staff, administrative staff, infectious disease panel, call center agents, subject matter experts, etc. associated with one or more of health care-related entities as described herein. For example, the stream of data may correspond to numerous patient care coordination and delivery systems, such as enterprise clinical and business workflow systems, pharmacy data warehouse systems, pharmacy transactional systems, laboratory information systems, drug and medical device databases, governmental healthcare organizations, etc. In some implementations, the data ingestion module 502 is coupled to the data storage 243 to process and store the stream of data as user profile data 302, electronic health records 304, pharmacy data 308, demographic data 310, appointment data 312, facility data 314, clinical data 316, geographic data 318, client device data 320, medical equipment data 322, application metadata 328, transaction data 330, workflow data 332, and other data 334 in the data storage 243.

The data ingestion module 502 receives a stream of user-generated data from one or more data channels or engagement channels. For example, a data channel may be associated with one or more of the client device 115 and the medical device 145. User-generated data collected from different data channels may include, but is not limited to, data collected from one or more of user interactions and user preferences on a healthcare-related application (e.g., email, messaging, calendaring, social networking, mobile health, video call, audio call, known allergies, etc.) running on a smartphone, a proprietary web or cloud application running on a client device 115 in a health care provider's office, a user wearable computing device tracking activity of a patient member, a medical device 145 monitoring vitals and health status information (e.g., heart rate, blood pressure, electrocardiogram, etc.) of a patient member, and other data stored on the plurality of third-party servers 140 that are connected over the network 105 to the client devices 115 and medical devices 145, etc.

The data ingestion module 502 receives a stream of clinical data, laboratory data, and retail pharmacy data associated with the plurality of patients. For example, the data ingestion engine 502 may query the plurality of data sources 243 for collecting the clinical data, laboratory data, pharmacy data, etc.

Clinical data may include, but is not limited to, EMR data, EHR data, patient-physician encounter data (e.g., name, age, phone number, temperature, pulse, weight, height, encounter date, encounter type, encounter reason, encounter location, encounter time, encounter physician notes, clinical condition assessment, patient criticality level rating, emergency department and outpatient reports, admission and discharge documentation, diagnostics, labs, imaging orders, vitals and health status information, etc.), patient demographics (e.g., gender, birth date, address, preferred language, ethnicity, marital status, religion, etc.), zip-code level demographics data, individual social determinant data (e.g., financial information, education level, mobility, race, alcohol use, tobacco use, drug use, etc.), patient surveys, patient problem list, patient medical history, patient medical charts, patient procedures (e.g., ICD procedure codes, procedure date, procedure results, etc.), physician appointment history, upcoming appointment data, patient diagnoses, patient criticality level assessment, medical laboratory test results data, hospitalization data, rehabilitation data, health plan data, Center for Medicare & Medicaid Services Hierarchical Condition Category (CMS-HCC) risk score, census data and other public data (e.g., clinical rules, empirical guidelines, recommended medications for different indications, treatment procedures, etc. published by subject matter experts (e.g., an infectious disease panel, etc.) belonging to a region, sub-region, medical center, governmental regulatory body, etc.), drug and medical device data (e.g., catalogue of prescription medication and medical device-related information approved by the Federal Drug Administration (FDA), etc.), etc.

Laboratory data may include, but is not limited to, patient member ID, laboratory test ID, laboratory test order ID, user ID of the healthcare personnel ordering the laboratory test, a timestamp when laboratory test was conducted, a timestamp when laboratory test result was published, a type of laboratory sample collected, a timestamp of sample collection, history of laboratory tests, recurring laboratory tests, laboratory service provider, laboratory technician ID, etc.

Pharmacy data may include, but is not limited to, prescription data, medication data (e.g., medication ID, date ordered, start and end date of medication administration by healthcare personnel, time of day of medication administration, number of medication administrations to the patient per day, member ID of the healthcare personnel administering the medication to the patient, medication dosage, medication cycling, etc.), pharmaceutical data, medication history, medication refills (e.g., number of refills, date and time of refill pick up, pharmacy technician ID who fulfilled the refill, etc.), medication adherence data, proportion of days covered (PDC) score, polypharmacy data, drug allergies, drug-drug interaction data, drug-bug interaction data, route of delivery (e.g., oral, intravenous, suppository, etc.), etc.

In some implementations, the data ingestion module 502 processes, correlates, integrates, and synchronizes the received data streams from disparate devices 115, 145, servers 140, and data sources 135 into a consolidated data stream to perform the functionalities as described herein. The data ingestion module 502 links the enterprise clinical and business workflow data obtained in association with a patient member (e.g., tracked through user identifier, triage session, etc.) to the transaction data 230 and the metadata 228 generated by one or more components of the care augmentation application 110 for the patient member. The data filtering module 506 described in detail below may use such linked data to perform its functionality as described herein.

In some implementations, the data ingestion module 502 processes, correlates, integrates, and synchronizes the received data streams from disparate devices 115, 145, servers 140, and data sources 135 along three axes, such as clinical care axis, patient historical care axis, and geographical care axis. The data organized along the clinical care axis may include the clinical data, laboratory data, pharmacy data, and/or a combination thereof. For example, the data ingestion module 502 aggregates and organizes data including clinical data, laboratory data, and pharmacy data for a patient admitted into a hospital and identifies a cohort of patients with similar data. The data organized along the historical care axis may include historical patient care data organized into different clinically coherent episodes of care, typically linked by diagnosis. An episode of care may be the patient's entire treatment undertaken for a particular illness. For example, for a patient suffering a heart attack, the episode of care may include everything done to diagnose and treat the condition grouped together into one clinically-defined episode of care. The data organized along the geographical care axis may include regional care pathway data for a patient and their cohorts. For example, the regional care pathway data may include care pathways in all stages of healthcare—from diagnosis of different diseases to treatment and follow-up-practiced in a regional hospital where patient resides and a regional hospital where the patient visits for care, in-network hospital of the patient's health insurance provider and out-of-network hospital of the patient's health insurance provider, and so on. The recommendation module 508 described in detail below may receive and use such processed data along the three axes to perform its functionality as described herein.

In some implementations, the data ingestion module 502 instantiates a data ingestion layer that transports data from assorted data sources 135 to the data storage 243 where it can be stored, accessed, and analyzed by the care augmentation application 110. For example, the data ingestion layer processes incoming data, prioritizes sources, validates individual files, and routes the data to the data storage 243. In some implementations, the data ingestion module 502 instantiates a data transformation layer that maps and converts data from a source format (e.g., of a data source 135) to a destination format. For example, the data transformation layer transforms non-XML data to XML data.

In some implementations, the data ingestion module 502 creates a user profile data 302 for a patient member based on processing the received data streams. The user profile 402 may include data and insights about the user including name, unique user identifier, age, gender, interests, height, weight, risk score, location, profile photo, recently measured vital signs, diagnosed health conditions (e.g., diabetic, mental health, heart attack, etc.), medical history, user preferences (e.g., a preferred healthcare provider, a preferred healthcare facility, a phone call for upcoming reminders, a video call for virtual urgent care visits, etc.), prescription (e.g., refill dates, etc.), laboratory test results, treatment or care plans, fitness goals (e.g., gain physical mobility, lose weight, etc.), activities (e.g. number of physical therapy sessions attended, number of missed appointments, synced wearable fitness devices, synced third-party mobile Health applications, etc.), etc. The data ingestion module 502 stores and updates the user profile data 302 in the data storage 243.

The NLP module 504 may include software and/or logic to provide the functionality for natural language understanding of medical conditions, disease indications, medications, medical procedures, etc. based on user input in the form of text, speech, or video. In some implementation, the NLP module 504 may be implemented for automated chart review of medical records of a patient member by the data ingestion module 502. For example, the NLP module 504 may process physician and nursing notes from a patient encounter and generate a natural language understanding of primary, secondary, and/or tertiary indication classifications associated with the diagnosis of the patient member. In another example, the NLP module 504 may process the physician notes from the patient encounter and generate a natural language understanding of a medication, dosage, schedule, route of delivery, etc. prescribed by a physician associated with the treatment of the patient member. The NLP module 504 is shown in broken lines to indicate that it is optional and the functionalities of the NLP module 504 as described herein may be performed by the machine learning module 510 and/or the recommendation module 508 instead. The NLP module 504 may automatically extract an indication, a location of the indication, a severity of the indication, a type of the indication, and a duration of suffering of the indication by a patient member from the physician notes recorded for the patient member during the encounter. For example, the NLP module 504 may process the physician notes and identify that a patient member has a "skin infection" of the type "cellulitis" on the "left ankle" for "three days" and that its severity or acuity level is "mild." The NLP module 504 may cooperate with the machine learning module 510 as described below in more detail. The NLP module 504 customizes the generation of natural language understanding responses for each of the healthcare personnel (e.g., physician, nurse practitioner, laboratory technician, etc.), patient, etc. In some implementations, the NLP module 504 receives request including the data for natural language understanding from the data ingestion module 502 and processes the request in cooperation with the machine learning module 510 to produce a natural language understanding response. The NLP module 504 then provides the response data back to the data ingestion module 502 for transmission to the computing device 120, and to the data storage 243 for storage. For example, the natural language response for processing the patient encounter data may be stored as application metadata 328 and transaction data 430.

The data filtering module 506 may include software and/or logic to provide functionality for filtering the data collected by the data ingestion module 502. In some implementations, the data filtering module 506 cooperates with the data ingestion module 502 and the user interface module 516 to filter the stream of data of a patient member and surface contextually relevant data to a healthcare personnel in a user interface on the client device 115 and/or medical device 145 to assist them in their decision making process for care delivery. In some implementations, the data filtering module 502 filters the stream of data associated with the patient member from the data ingestion module 502 that satisfy a predetermined threshold. For example, the data ingestion module 502 extracts one or more biomarkers of interest (e.g., white blood count, cholesterol, platelets, hemoglobin, glucose, creatinine, etc.) from results of laboratory tests done for a patient member that satisfies a threshold value and filters out the rest of the stream of data. In some implementations, the data filtering module 502 filters the stream of data associated with the patient member consolidated on a predetermined boundary of time that satisfy a predetermined threshold. For example, the data filtering module 502 extracts a peak in vitals (e.g., temperature, respiration rate, blood pressure, etc.) on a 1-minute, 15-minute, 30-minute, 1-hour, or 24 hour boundaries that satisfies a threshold value and filters out the rest of the stream of data. The data filtering module 506 cooperates with the user interface module 516 to generate a clinical dashboard for managing the care of a plurality of patient members in a stewardship workflow. For example, the clinical dashboard may be referred to as a "patient-on-a page" dashboard that contextually presents the filtered patient information from disparate data sources as described herein. The filtered patient information may along the clinical care axis, historical care axis, and geographical care axis that include healthcare personnel notes, patient vitals trend, patient medication timeline, patient laboratory results, an activity log associated with the treatment of the patient within the workflow of the stewardship program, etc.

The data filtering module 506 may receive a request from a healthcare personnel to tag and track filtered information of a patient member from the plurality of patient members under care in a stewardship workflow. For example, a nurse practitioner may tag a patient's name in the clinical dashboard to receive alert notification for preliminary results of a bacterial culture test ordered in the workflow of the antibiotic stewardship program. The data filtering module 506 filters the incoming stream of data of the tagged patient, identifies the requested preliminary results becoming published by the laboratory technician, and surfaces a notification alert in association with the patient's name indicating the availability of the preliminary results. The data filtering module 506 may cooperate with the machine learning module 510 as described below in more detail. The data filtering module 506 tracks a patient member (e.g., through user identifier, triage session, etc.) and filters the stream of data associated with the patient member in cooperation with the machine learning module 510.

The machine learning module 510 may include software and/or logic to provide functionality for generating training datasets and training one or more machine learning models 326 or classifiers using the training datasets. In some implementations, the machine learning module 510 may curate one or more training datasets 324 based on the data received and processed in association with a plurality of the client devices 115, the medical devices 145, the healthcare management server 120, the third-party servers 140, and the data sources 135 by the data ingestion module 502. For example, the machine learning module 510 receives the patient EMR data including physician notes, cleans the data, and derives sample historical and curated text or speech utterance data (words, phrases, sentences, etc.) associated with primary, secondary, and tertiary indications associated with a plurality of patient members for generating the training datasets 324. Other example training datasets 324 curated by the machine learning module 510 may include, but not are limited to, a dataset of clinical care (e.g., EMR data, EHR data, clinical conditions, comorbidities, diagnoses, encounter data, vitals, medications, drug allergies, laboratory results, treatments, procedures, imaging test results, etc.) for a plurality of patient members and their cohorts, a dataset including historical care data (e.g., historical hospitalization data, historical rehabilitation data, historical admission, treatment, and discharge documentation, medication history, prior episodes of care, existing health risks, recurring infections, annual physical assessments, preventive screening, vaccinations, etc.) of a plurality of patients and their cohorts, a dataset of regional care pathways (e.g., empirical guidelines, care plans, stewardship workflows, clinical research, clinical studies, etc. for different diseases) implemented in different geographical locations (e.g., region, sub region, medical centers, county, state, country, etc.) for a plurality of patients and their cohorts, a dataset of primary, secondary, and tertiary indications for a plurality of patients and corresponding medications, dosage, and route of delivery as labelled output to predict, a dataset of laboratory test results and medication as labelled output to predict for a plurality of patients, a dataset of condition identification and/or criticality level identifications hints and patterns for a plurality of patients and their cohorts, a dataset of care event identifications hints and patterns for a plurality of patients and their cohorts, a dataset of medical dictionary terms and indexed search terms and an actual criticality level for those terms, a dataset of treatments for a plurality of patients and their cohorts in a stewardship program, any combination of datasets thereof, etc.

In some implementations, the machine learning module 510 may create a crowdsourced training dataset 324. For example, in the instance where a user (e.g., patient member) consents to use of their data for creating a training dataset, the machine learning module 510 forwards the aggregated data to remotely located reviewers (e.g., physicians, nurse practitioners, subject matter experts, etc.) to review the data, identify a segment of the data, classify and provide a label for the identified data segment. The machine learning module 510 stores the curated training datasets 324 in the data storage 243. The machine learning module 510 uses the training datasets 324 to train the machine learning models 326 for performing the various functionality as described herein. The machine learning module 510 stores the trained machine learning models 326 in the data storage 243.

The machine learning module 510 creates one or more machine learning models 326 for use by the NLP module 504, the data filtering module 506, and the recommendation module 508 (described in detail below) based on training them using the curated datasets. For example, the machine learning model 326 may be a trained NLP model 326 that is able to extract primary, secondary, and/or tertiary indications associated with a health condition based on classifying user input utterance (e.g., text or speech) of a healthcare personnel in their notes taken during a patient encounter. In another example, the machine learning model 326 may be a neural network model that is able to classify one or more of patient member profile, encounter data, past medical and clinical history, demographic data, etc. to infer the likely level of criticality of a patient's health in a workflow. The machine learning module 510 generates one or more machine learning models 326 for supporting multi-lingual input classification. For example, the NLP models may be trained to be native language-specific and extended to support multilingual user inputs in English, Spanish, Vietnamese, Russian, etc. In another example, the machine learning module 510 generates machine learning models 326 for performing language translation of user inputs. In yet another example, the machine learning module 510 uses a combination of language-specific models and language translation models.

The machine learning module 510 facilitates providing input necessary to create a particular machine learning model 326. In some implementations, the machine learning module 510 receives and/or generates data, models, training data, and scoring parameters necessary to create the machine learning model 326. For example, the machine learning module 510 may provide curated multilingual text inputs, provide criticality level identification and/or health condition identification hints and patterns, provide care event identification hints and patterns, provide treatment identification hints and patterns, provide model negators, perform training, testing, approve, and publish model versions for consumption, perform scoring model parameter tuning, or create scoring accuracy thresholds for generating a machine learning model 326. The machine learning module 510 is adapted to receive input from users, such as healthcare personnel, data scientists, analysts, or engineering staff to define and enhance the machine learning models 326. The machine learning module 510 may provide a secure portal through which these users may define, train, test, publish, refine, retrain, and improve the machine learning models 326 or introduce new models. For example, the portal may be used to define, train, test and publish NLP models for identification of primary, secondary, and/or tertiary indications from the physician notes about a patient member. The portal allows the users to provide training data-text inputs or spoken word utterances, multi-lingual input, synonyms, conjugation, typos, mispronunciations, model negators, etc. The portal enables the users to define hyperparameters of a machine learning model 326 to fine tune the output, such as criticality level assessment, etc. and modify scoring thresholds. The portal allows users to enhance the models during training using machine learning hints, patterns, and/or phrases. The portal further enables the users to control or reduce the overlap of inputs between classes of criticality levels during the training of a machine learning model 326.

In some implementations, the machine learning module 510 emphasizes certain sets of features, traits or attributes in a machine learning model 326 during training for improving recognition, accuracy, computational speed, etc. For example, the machine learning models 326 may be trained based on the following features or attributes, including but not limited to: patient member profile (age, gender, location, race, socioeconomic, user preferences, etc.); patient member clinical context (e.g., past and current health conditions, medications, allergies, laboratory results, treatments, historical encounter data, current encounter data, etc.); medical terms and dictionary; or statistics of input text, predicted criticality levels, predicted care events, proposed and actual dispositions, proposed medications and alternative medications, etc.

The machine learning module 510 creates one or more machine learning models 326 for the recommendation module 508 (described in detail below) to identify and surface one or more of treatment plans, prescription medications, alert notifications, custom visualizations of patient data, etc. to healthcare personnel providing a stewardship of care. For example, the machine learning module 510 trains one or more machine learning models using features, such as patient care clinical data, patient historical data, contextual regional care pathway data (e.g., geographical evidence based guidelines, treatment data associated with a similar cohorts of patients in a different medical center, region, sub-region, county, state, country, etc.), etc. to output a recommendation for a healthcare personnel. The machine learning module 510 provides the machine models 326 to the data storage 243 for storage. In some implementations, the machine learning models 326 may be stored as part of application metadata 328 and transaction data 330 in the data storage 243.

In some implementations, the machine learning module 510 may be configured to incrementally adapt and train the one or more machine learning models 326 every threshold period of time. For example, the machine learning module 510 may incrementally train the machine learning models 326 every hour, every day, every week, every month, etc. based on the aggregated dataset from the data ingestion module 502 and aggregated expert feedback from the expert correction module 508. In some implementations, a machine learning model 326 is a neural network model and includes a layer and/or layers of memory units where memory units each have corresponding weights. During training of the neural network model, the machine learning module 510 adjusts the numerical values associated with connections between neurons in the neural network, essentially controlling how much influence each input feature has on the final prediction, thus allowing the neural network model to learn and improve its accuracy by fine-tuning its response to different data patterns during the training process. A variety of neural network models may be utilized including feed forward neural networks, convolutional neural networks, recurrent neural networks, radial basis functions, other neural network models, as well as combinations of several neural networks. Additionally, or alternatively, the machine learning model 326 may represent a variety of other machine learning techniques in addition to neural networks, for example, support vector machines, decision trees, Bayesian networks, random decision forests, k-nearest neighbors, linear regression, least squares, hidden Markov models, other machine learning techniques, and/or combinations of machine learning techniques. In some implementations, the machine learning module 510 uses keyword-based database lookups, or search by keywords and clinical terms to implement training of one or more machine learning models 326.

In some implementations, the machine learning module 510 may train one or more machine learning models 326 to perform a single machine learning task or a variety of machine learning tasks. In other implementations, the machine learning model 326 may be trained to perform multiple tasks. In yet other implementations, the machine learning module 510 may train a machine learning model 326 to receive the requested data and generate the response data.

The machine learning module 510 determines a plurality of training instances or samples from the training dataset 324. The machine learning module 510 may apply a training instance as input to a machine learning model 326. In some implementations, the machine learning module 510 may train the machine learning model 326 using any one of at least one of supervised learning (e.g., support vector machines, neural networks, logistic regression, linear regression, stacking, gradient boosting, etc.), unsupervised learning (e.g., clustering, neural networks, singular value decomposition, principal component analysis, etc.), or semi-supervised learning (e.g., generative models, transductive support vector machines, etc.). Additionally, or alternatively, machine learning models 326 in accordance with some implementations may be deep learning networks including recurrent neural networks, convolutional neural networks (CNN), networks that are a combination of multiple networks, etc. The machine learning module 510 may generate a predicted machine learning model output by applying training input to the machine learning model 326. Additionally, or alternatively, the machine learning module 510 may compare the predicted machine learning model output with a known labelled output from the training instance and, using the comparison, update one or more weights in the machine learning model 326. In some implementations, the machine learning module 510 may update the one or more weights using an optimization algorithm including backpropagation that adjusts the weights in a direction that minimizes the difference over the entire machine learning model 326.

In some implementations, the machine learning module 510 may test a trained machine learning model 326 and update it accordingly. The machine learning module 510 may partition the training dataset 324 into a testing dataset and a training dataset. The machine learning module 510 may apply a testing instance from the training dataset 324 as input to the trained machine learning model 326. A predicted output generated by applying a testing instance to the trained machine learning model 326 may be compared with a known output for the testing instance to update an accuracy value (e.g., an accuracy percentage) for the machine learning model 326. For example, the machine learning module 510 analyzes the accuracy scores of classifying various indications by a NLP model. In some implementations, the machine learning module 510 may version and service the model 326 through an internal HTTP endpoint to be used by other component(s) of the care augmentation application 110. For example, once a model 326 is trained and tested and determined to have acceptable accuracy (e.g., accuracy score satisfying a threshold), the machine learning module 510 pushes the model 326 to the NLP module 504 and the recommendation module 508 to consume for identifying indications (implemented as natural language understanding (NLU) text classification) and performing criticality level assessment, among other things. In some implementations, model development is an iterative process with retraining, testing and publishing steps performed iteratively, and adapted automatically to improve scores and accuracy. New versions will be published based on improvements and retraining using historical data and efficiency calculations as more data including expert correction is collected over a period of time. For example, the NLP model or classifier class labels requires clinical and business oversight and will be promoted for usage by capability based on clinical and business review. Continuous retraining using training data (utterances, phrases, hints, negators, language variants, expert correction, etc.) are performed based on curation as part of clinical and data analysis.

In some implementations, the machine learning module 510 generates a variety of metadata 328 in association with model training and deployment. For example, the metadata 328 includes: criticality levels and/or care events to be identified from models 326, scoring thresholds for these criticality levels and/or care events, notification urgency to be associated for these criticality levels and/or care events, and other training metadata and parameters. The machine learning module 510 stores into and serves the metadata 328 from the data storage 243.

The recommendation module 508 may include software and/or logic to provide functionality for generating a recommendation for facilitating the decision making of a healthcare personnel when they are executing the healthcare practices and delivery workflows of the healthcare steward-ship program. For example, the healthcare stewardship program may include, but is not limited to, an antibiotics/antimicrobial stewardship program, atrial fibrillation (AFIB) care stewardship program, neuro deep brain stimulation stewardship program, asthma exacerbation care stewardship program, chronic obstructive pulmonary disease (COPD) care stewardship program, vascular disease (e.g., atheroscle-rosis) care stewardship program, cancer care stewardship program, autoimmune disease (e.g., diabetes, arthritis, mul-tiple sclerosis, etc.) care stewardship program, chronic kid-ney disease care stewardship program, etc. The recommen-dation module 508 may use one or more machine learning models 326 to optimize healthcare practices and care deliv-ery in stewardship workflows along the lines of consistency of care (e.g. increase consistency of care), regulatory com-pliance (e.g., increase regulatory compliance), costs (e.g., decrease healthcare costs), gap in care (e.g., decrease the gap in care), cognitive burden (e.g., decrease cognitive burden of the healthcare personnel), etc. with the generation of the recommendations. For example, the recommendation mod-ule 508 uses one or more trained machine learning models 326 generated by the machine learning module 510 to generate the recommendations that standardize the health-care service practices, increase the quality of care for patients, improve the workflow efficiency of healthcare personnel, reduce the costs associated with providing health-care services, and enable the ease of regulatory compliance. In some implementations, the recommendation module 508 generates a recommendation that includes a rating (e.g., confidence score) and a source (e.g., empirical source or learned). For example, the recommendation may include a patient criticality level, a care event of interest, a treatment, etc. The healthcare personnel may review the recommenda-tion and perform an action in the workflow, such as accept-ing, rejecting, or changing the recommendation.

In some implementations, the recommendation module 508 in cooperation with the data ingestion module 502, the NLP module 504, the data filtering module 406, and the machine learning module 510 may process the filtered stream of data and other persisted data of a patient member in the data storage 243 as described herein for generating a recommendation. This recommendation may be presented to a patient member and/or a healthcare personnel associated with the patient member. For example, the filtered stream of data and the other persisted data of the patient member in the data storage 243 may be along one or more of clinical care axis, patient historical care axis, and geographical care axis. Subject matter experts may get together on a frequent basis to identify variances in thresholds and trends associated with indications (e.g., a sign, symptom, or medical condition that leads to the recommendation of a treatment, test, and/or procedure) observed in a localized geographical area (e.g., a region, a sub-region, a county, a medical center, etc.) and standardize care for treatment, test, or procedures of each of the indications for patient members treated in that localized geographical area. The variations and trends associated with indications may also be observed across ethnicities, gender, age, demographics, people with preexisting health condi-tions (e.g., diabetes, cancer, hypertension, etc.), etc. For example, there may be variances in threshold levels associ-ated with white blood count, creatinine, body temperature, etc. The recommendation module 508 may be configured to accommodate the local variances in treatments, tests, and/or procedures as identified by the subject matter experts as one of several inputs to weight appropriately in a trained machine learning model 326 and accordingly generate the recommendations for optimizing the healthcare practices and delivery workflows in a stewardship program. Health-care personnel may also follow empirical guidelines asso-ciated with the treatment, test, and procedures for treating indications observed in patient members in a localized geographical area. The recommendation module 508 may be configured to accommodate the empirical guidelines as one of several inputs to weight appropriately in the trained machine learning model 326 and accordingly generate the recommendations for optimizing the healthcare practices and delivery workflows in a stewardship program.

The recommendation module 508 determines a recom-mendation in association with a delivery of care to the patient member by processing the patient member data along one or more of clinical care axis, patient historical care axis, and geographical care axis, such as clinical data (e.g., EHR data, etc.), indications extracted using NLP from physician notes, laboratory test results including one or more biomark-ers, vitals, pharmacy data (e.g., patient medication history, medication adherence, etc.), patient treatment history, aller-gies, comorbidities (e.g., diabetes, hypertension, etc.), pre-existing patient diagnoses (e.g., cancer patient, stroke sur-vivor, etc.), patient member profile (e.g., age, gender, ethnicity, demographic data, etc.), regional care data (e.g., regional care pathways and evidence-based guidelines in a geographical area where the patient is treated, etc.), etc.

In some implementations, the recommendation module 508 may process the patient member data using a trained machine learning model 326 and assign a criticality level to the patient member with an accuracy or classification score. For example, the criticality level may range from level zero (lowest criticality) to level four (highest criticality). In another example, the criticality level may be assigned as low, medium, and high. In some implementations, the recommendation module 508 may analyze and weigh several features associated with the patient member to determine a criticality level of the patient member undergoing treatment within a stewardship workflow. The recommendation module 508 may weigh the following features including but not limited to patient member profile and demographic data (e.g., age, gender, ethnicity, etc.); patient member's past medical history (e.g., known medical conditions, prescribed medications, laboratory and imaging results, etc.); patient's recent and current healthcare appointments, physician encounters and visit data; geographical location (e.g., place of residence, place of hospital admission, etc.), time of medical events (e.g., recent and current events), disease severity, disease frequency, comorbidities (e.g., cancer, heart attack survivor, etc.), drift between past critical level predictions and actual criticality dispositions; etc. For example, if the patient member has comorbidities, such as high blood pressure, type 2 diabetes, etc. and above the age of 50, the recommendation module 508 assesses a high level of criticality to the patient member for notifying the healthcare personnel. The recommendation module 508 may determine that the healthcare personnel is waiting on an update to the patient member data in the healthcare management server 120 and accordingly assess a criticality level rating to associate with the patient member. For example, the recommendation module 508 may assess a high criticality level to a patient if the healthcare personnel has ordered a biopsy test and is waiting on the laboratory results.

The recommendation module 508 may further modify the weighting for criticality level assessment based on relevance hints and rules as provided by healthcare personnel, such as physicians and other clinical staff (e.g., based on clinical and regulatory requirements). The criticality level may refer to the severity of the potential health condition and the level of attention that the patient member requires from a health care personnel. In one example, a criticality level of zero may be associated with a patient member who is young, alert, undergoing an out-patient visit for a routine health check-up, having normal vitals, normal biomarkers in laboratory test results, etc. In another example, a criticality level of one may be associated with a patient member having a single indication, under observation post-surgery with no change in vitals, etc. In another example, a criticality level of two may be associated with a patient member having multiple indications, normal vitals, pending laboratory tests, pending medication change, etc. In yet another example, a criticality level of three may be associated with a patient member having multiple indications, varying vitals throughout the day, under observation for a week or more, pending multiple laboratory tests, etc.

The recommendation module 508 surfaces the recommendation to a healthcare personnel in a clinical dashboard to reduce the cognitive burden in the decision making process. The recommendation module 508 cooperates with the user interface module 516 to generate and sort a listing of a plurality of patients in a stewardship workflow on the clinical dashboard based on their assessed levels of criticality. For example, the plurality of patients may be ranked in a descending order of criticalities—the patient with the highest level of criticality at the top of the listing and the patient with the lowest level of criticality at the bottom of the listing. Such a ranking may help the healthcare personnel to easily find the patient member needing their immediate attention and care from among the plurality of patients in the stewardship workflow. The recommendation module 508 may also associate a graphical indicator with a patient in the listing of the plurality of patients to indicate a status associated with a review of the patient by a healthcare personnel in the stewardship workflow. For example, the graphical indicator may be a bold exclamation mark in red next to the patient's name to alert the healthcare personnel to review the treatment strategy of the patient. In another example, the graphical indicator may change from the red exclamation mark to a green tick mark next to the patient's name to indicate that the healthcare personnel has completed a review of the treatment strategy of the patient.

The recommendation module 508 in cooperation with the data filtering module 506 may identify and surface relevant healthcare data of the patient member that is likely to impact the decision making process of the healthcare personnel providing the stewardship of care to the patient member in a corresponding stewardship workflow. For example, the healthcare data that may be relevant to the healthcare personnel is a care event of interest. A care event of interest may be any significant occurrence or action taken within a patient's journey, such as a diagnosis change, a medication change, an availability of a laboratory test result, an intensive care unit admission, a discharge to ward, a change (e.g., peak or bottom) in vitals, a change (e.g., presence or absence) in biomarkers, or any significant change in health status during treatment which needs to be brought to the attention of relevant healthcare personnel to allow them to monitor and manage the patient's care effectively.

In some implementations, the recommendation module 508 generates an alert notification relating to an update in the patient member health data from the filtered stream of data and pushes the alert notification to the healthcare personnel. There is a challenge in that anytime a result or update in a patient's health data is output, there is a system-generated notification (e.g., by EMR/EHR record systems) for the corresponding healthcare personnel. It may be detrimental to generate an alert notification for every update in a patient member's EMR, such as change in vitals, prescription medication, laboratory tests, etc. If there is a generation of an alert notification for every update, and that too for hundreds of patients at a facility for a stewardship program, it may result in an alert fatigue and overwhelm the healthcare personnel. In some implementations, the recommendation module 508 uses a trained machine learning model on the filtered stream of data to identify a notification that is relevant to the delivery of care to the patient member by a healthcare personnel. In some implementations, the recommendation module 508 may determine a criticality and/or an urgency associated with the update in the patient member health data and issue an alert notification to the healthcare personnel based on the criticality and/or urgency. For example, the recommendation module 508 may identify that a laboratory test result for a biopsy of a patient member is urgent that is to be brought to the immediate attention of a healthcare personnel and generate an alert notification accordingly. In another example, the recommendation module 508 may identify that a urine test screening for comorbidities of a patient member admitted for a lung infection is not urgent and generate a delayed notification alert for the healthcare personnel. In some implementations, the recommendation module 508 may rank the care events of interest generated for a plurality of patient members and generate an alert notification to the healthcare personnel based on the ranking. The recommendation module 508 may also identify a type of healthcare personnel to notify and send the alert notification regarding the care event of interest in the patient member health data. For example, the recommendation module 508 may send an alert notification of a preliminary result of a patient member's bacteria culture test to an in-hospital nurse practitioner executing a workflow of the antibiotic stewardship on the weekend rather than to the infectious disease specialist or the physician in-charge who may be absent on the weekend.

The recommendation module 508 may generate a recommendation of a treatment associated with a patient member for review by the healthcare personnel within the workflow. For example, the recommendation of a treatment may include but not limited to a therapeutic procedure, a surgical procedure, a non-surgical procedure, a laboratory test, a medical test, an imaging test, a medication prescription, a follow-up care, etc. The recommendation module 508 uses a machine learning model 326 trained on the user behavior of the healthcare personnel that instruments their behavior and improves efficiency of care delivery workflow. For example, the machine learning model may be trained on historical healthcare personnel data including user preferences for specific treatments, certain laboratory tests, particular medication prescriptions, etc. per indication, per severity level, per laboratory test results, per threshold patient vitals, etc.

In some implementations, the recommendation module 508 may process the patient member data using a trained machine learning model 326 and recommend a medication, a dosage of the medication, and route of delivery of the medication for administering to the patient member with an accuracy or classification score. For example, the recommendation module 508 may check whether the indication extracted from the physician notes is in alignment with a medication prescribed for the patient member as per empiric guidelines. If there are not in alignment, the recommendation module 508 may recommend a new prescription medication. If there are in alignment, the recommendation module 508 may recommend no change in the medication. In another example, the recommendation module 508 may check whether the antibiotic medication prescribed for the patient member is at the end of its life based on empirical guidelines and biomarkers observed in the patient data and recommend a change in antibiotic medication for the healthcare personnel to consider. In another example, the recommendation module 508 may check whether a prescription medication for the patient member is a good match based on allergies, unsafe combinations with exiting prescription medication (e.g., drug-drug interaction) of the patient member, inefficacy due to a bug becoming resilient in the geographical location (e.g., drug-bug interaction), etc. and recommend a change in the prescription medication. In some implementations, the recommendation module 508 may process the patient member data using a trained machine learning model 326 and recommend a treatment plan for the patient member with an accuracy or classification score. For example, the recommendation module 508 may check to see if the patient member data matches with a treatment plan tailored to the specific medical center where the patient member is admitted. If the treatment plan of a medical center at a different geographical location instead matches with the patient member data, then the recommendation module 508 may recommend the alternative treatment plan for the healthcare personnel to consider and approve for the patient member. For example, assume a first patient at a first medical center is observed to have responded to an increased dosage and intravenous delivery of an antibiotic X for an infection. When a second patient at a second medical center is admitted with the same immune profile and infection as the first patient, the recommendation module 508 may recommend the same increased dosage and intravenous delivery of the antibiotic X for the second patient even if the care pathway guidelines at the second medical center differ and suggest a reduced dosage and oral delivery for the antibiotic X.

In some implementation, the recommendation module 508 automatically administers the treatment to the patient if the criticality level assessed for the patient is low. For example, a patient with low level of criticality has a low risk of health outcomes. If the criticality level assessed for the patient is medium, the recommendation module 508 follows the preference of the healthcare personnel for treatment administration. For example, for those patients with medium criticality level that the healthcare personnel has opted for automatic dispensing of treatment, the recommendation module 508 automatically administers the treatment. If the criticality level assessed for the patient member is high, the recommendation module 508 surfaces the recommendation to the healthcare personnel for review and administration of the treatment.

The expert correction module 512 may include software and/or logic to provide functionality for analyzing the effectiveness of machine learning models 326 and optimizing them based on the analysis. In some implementations, the expert correction module 512 is coupled to receive and analyze the operational machine learning models 326 used by the recommendation module 508, the NLP module 504 and the data filtering module 506. The expert correction module 512 is coupled to the data storage 243 to retrieve the metadata 228, the transaction data 230, and the workflow data 232 generated by the components of the care augmentation application 110. The expert correction module 512 uses the metadata 328, the transaction data 330, and the workflow data 332 to analyze the effectiveness and the quality of the models 326. The expert correction module 512 is also capable of providing a secure portal to allow data scientists, analysts, engineering staff, healthcare personnel, etc. to provide feedback or correction for a generated model output which is then used to improve the accuracy of the models 326 via retraining. The expert correction module 512 may receive and process the user action of a healthcare personnel in the user interface (UI) of the clinical dashboard in response to the recommendations. For example, the expert correction module 512 may receive a user action including a correction of an indication extracted by the NLU model from the physician notes. In another example, the expert correction module 512 may receive a rejection of a recommended prescription medication output by the recommendation module 508 and an input of a different prescription medication from the physician. In another example, the expert correction module 512 may receive an upgrade or downgrade of the recommended criticality level output by the recommendation module 508 from the physician for a patient member under observation. In yet another example, the expert correction module 512 may receive a selection of an alert notification for a first care event of interest and a dismissal of an alter notification for a second care event of interest from the nurse practitioner.

The expert correction module 512 determines one or more metrics for evaluating the quality of operational machine learning models 326 used by the recommendation module 508, the NLP module 504 and the data filtering module 506. For example, the expert correction module 512 determines several metrics including accuracy, precision, and recall of the output predicted by the operational models 326 based on the actions of the healthcare personnel moving forward with the recommendation for assessing the criticality level, accepting a prescription medication recommendation for treatment, and notifying a healthcare personnel about care events of interest. This analysis serves as input to creating new models 326 or retraining models 326 which may be subject to clinical oversight before deployment for use.

The expert correction module 512 may also facilitate with refining of model training data and machine learning hints, scoring thresholds, etc. identified through the analytics process. The expert correction module 512 sends data regarding the refinements to the machine learning module 510 as input into updating models 326 in an iterative process. For example, the expert correction module 512 generates a data snapshot of all healthcare data related to the patient member (for whom the recommendation of a criticality level, care event, and treatment was corrected, accepted, or rejected by the healthcare personnel) including indications, age, gender, comorbidities, indications, ethnicity, duration of treatment, medication, medication dosage, medication route, vitals, laboratory results, biomarkers, etc. and sends the data snapshot to the data ingestion module 502 and machine learning module 510 for updating the curated datasets. The machine learning module 510 uses the updated datasets to refine the models 326 for use by the NLP module 504, the recommendation module 508 and the data filtering module 506.

The compliance module 514 may include software and/or logic to provide functionality for recording user activity in association with the healthcare practices and delivery workflows of the healthcare stewardship program followed by the healthcare personnel for patient members. This may be done for auditing purposes. For example, the compliance module 514 records a log of recent activity in association with the patient treatment in an antibiotic stewardship workflow including but not limited to a running count of clear indications diagnosed at a visit, preliminary bacteria culture results, full culture results, a hospital center where the patient member was admitted, a history of every action, alert, request, notification, and other data or activity that came in. In another example, the compliance module 514 records a complete instrumentation of the entire healthcare practices and delivery workflow itself for the time the patient member was treated at the hospital.

In some implementations, the compliance module 514 processes the recent activity and performs episode of care groupings in cooperation with the data ingestion module 502. For example, the compliance module 514 tracks a patient history to identify whether the patient member was already in the hospital with the same bacterial, viral or fungal infection a week ago, a month ago, or a year ago and surface that episode of care grouping for compliance and consistency in the healthcare practices and delivery workflow. In some implementations, the compliance module 514 tracks every action that a user is taking in the delivery of care to a patient member while interacting with the care augmentation application 110. For example, the compliance module 514 builds knowledge that indicates when a patient member was admitted, when the physician's notes about the patient encounter were reviewed, when the patient member's vitals were checked, when was the laboratory test results reviewed by an attending healthcare personnel, what was the recommended action for treatment (e.g., medication change) generated by the system, when was the recommended action reviewed by a healthcare personnel, what action was actually performed by the healthcare personnel, how did the action differ from the recommended action, etc.

The user interface module 516 may include software and/or logic for providing user interfaces to a user. In some implementations, the user interface module 514 receives instructions from the components 502, 504, 506, 508, 510, 512, and 514, generates a user interface according to the instructions, and transmits the user interface for display on the client device 115. In some implementations, the user interface module 514 sends graphical user interface data to an application (e.g., a browser) in the client device 115 via the communication unit 241 causing the application to display the data as a graphical user interface.

Figure 6:
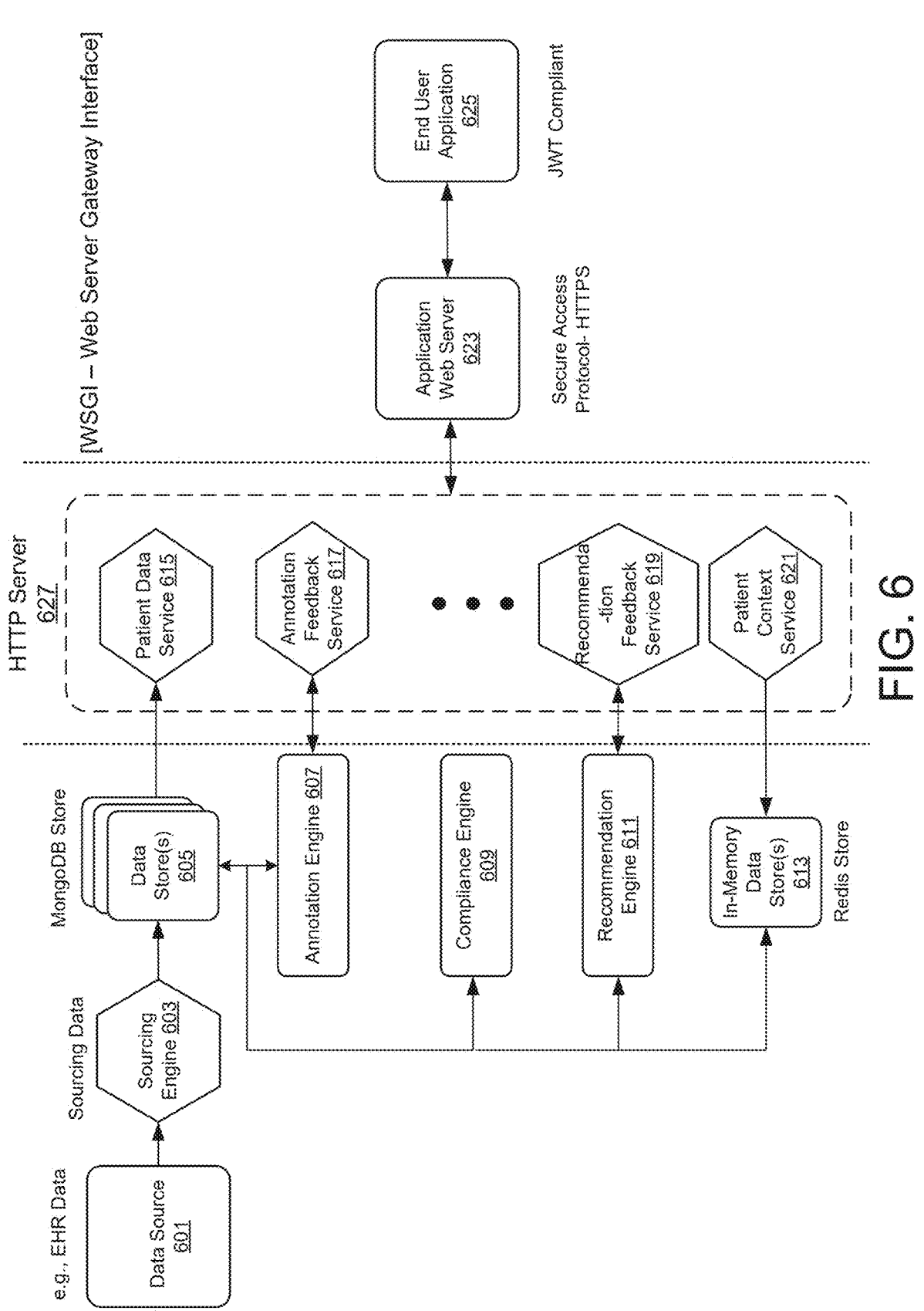
FIG. 6 is a block diagram illustrating one implementation
of a global system for facilitating a member journey through
healthcare service by augmenting stewardship workflow
across multiple service areas.

FIG. 6 is a block diagram illustrating one implementation of a global system for facilitating a member journey through healthcare service by augmenting stewardship workflow across multiple service areas. The sourcing engine 603 digitally connects to the data source 601 of streaming patient data, such as EHR data, pharmacy data, clinical data, laboratory data, etc. and pulls the data for aggregating in one or more data store(s) 605. The sourcing engine 603 may be functionally similar to the data ingestion module 502 as described herein. The sourcing engine 603 may implement a structured query language (SQL), a web service description language (WSDL), and/or health level seven (HL7) interface for sourcing the data from the data source 601 into the one or more of the data stores(s) 605 and in-memory data store(s) 613. For example, the data store(s) 605 may be a document storage or database to store physician notes, surgical notes, etc. In another example, the in-memory data store 613 may be database or cache to store key-value pairs, age, patient demographic data, weight, JSON objects, etc. The HTTP server 627 may be a representative of the healthcare management server 120 as described herein. In some implementations, another instance (not shown) of the sourcing engine 603 may be used to source the data from the data store(s) 605 and in-memory data store(s) 613 and feed it into the HTTP server 627 and any service running on the HTTP server 627. The HTTP server 627 may include micro-applications, such as a patient data service 615, an annotation feedback service 617, a recommendation feedback service 619, and patient context service 621 running in the background. The patient data service 615 may be functionally similar to the data filtering module 506 as described herein to filter the patient data. The annotation feedback service 617 may be functionally similar to the expert correction module 512 to receive feedback from the users that correct a recommendation output generated by one or more trained machine learning models 326 used by the recommendation module 508. The recommendation feedback service 619 may be functionally similar to the expert correction module 512 to receive feedback from the users that either accept or reject the recommendation generated by one or more trained machine learning models 326 used by the recommendation module 508. If rejected, the feedback includes the alternative decision made by the user. The application web server 623 may facilitate an application programming interface to decouple the end user application 625 from the HTTP server 627 running the micro-applications. The application web server 623 implements a secure access protocol (e.g., HTTPS) to maintain privacy and authenticate security credentials of authorized users of a healthcare organization accessing the HTTP server 627 via the end user application 625. For example, the end user application 625 may be enabled for doctors, nurses, pharmacists, etc. of a medical center. The end user application 625 may be functionally similar to the care augmentation application 110 as described herein. The end user application 625 may be a JSON Web Token (JWT) compliant.

Figure 7:
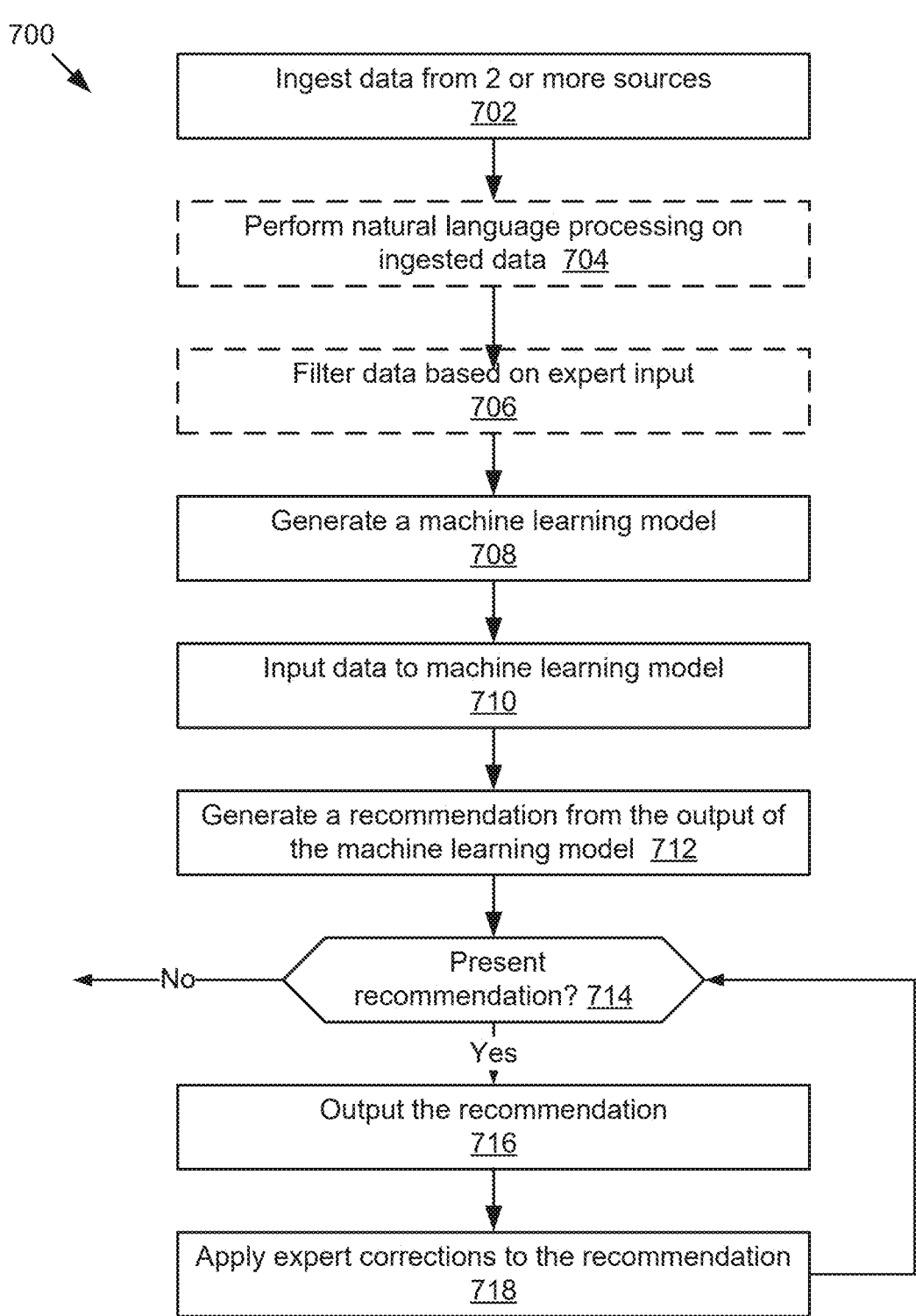
FIG. 7 is a flow diagram illustrating one implementation
of an example method for generating a recommendation for
augmenting a stewardship workflow.

FIG. 7 is a flow diagram illustrating one implementation of an example method 700 for generating a recommendation for augmenting a stewardship workflow. At 702, the care augmentation application 110 ingests data from two or more sources. At 704, the care augmentation application 110 performs natural language processing on ingested data. At 706, the care augmentation application 110 filters data based on expert input. At 708, the care augmentation application 110 generates a machine learning model. At 710, the care augmentation application 110 inputs data to machine learning model. At 712, the care augmentation application 110 generates a recommendation from the output of the machine learning model. At 714, the care augmentation application 110 determines whether to present the recommendation. If yes, at 716, the care augmentation application 110 outputs the recommendation. At 718, the care augmentation application 110 applies expert correction to the recommendation.

FIGS. 8-17 show graphical representations of example user interfaces for a care and clinical dashboard providing access to care relevant and fact-based intelligence according to some implementations.

Figure 8:
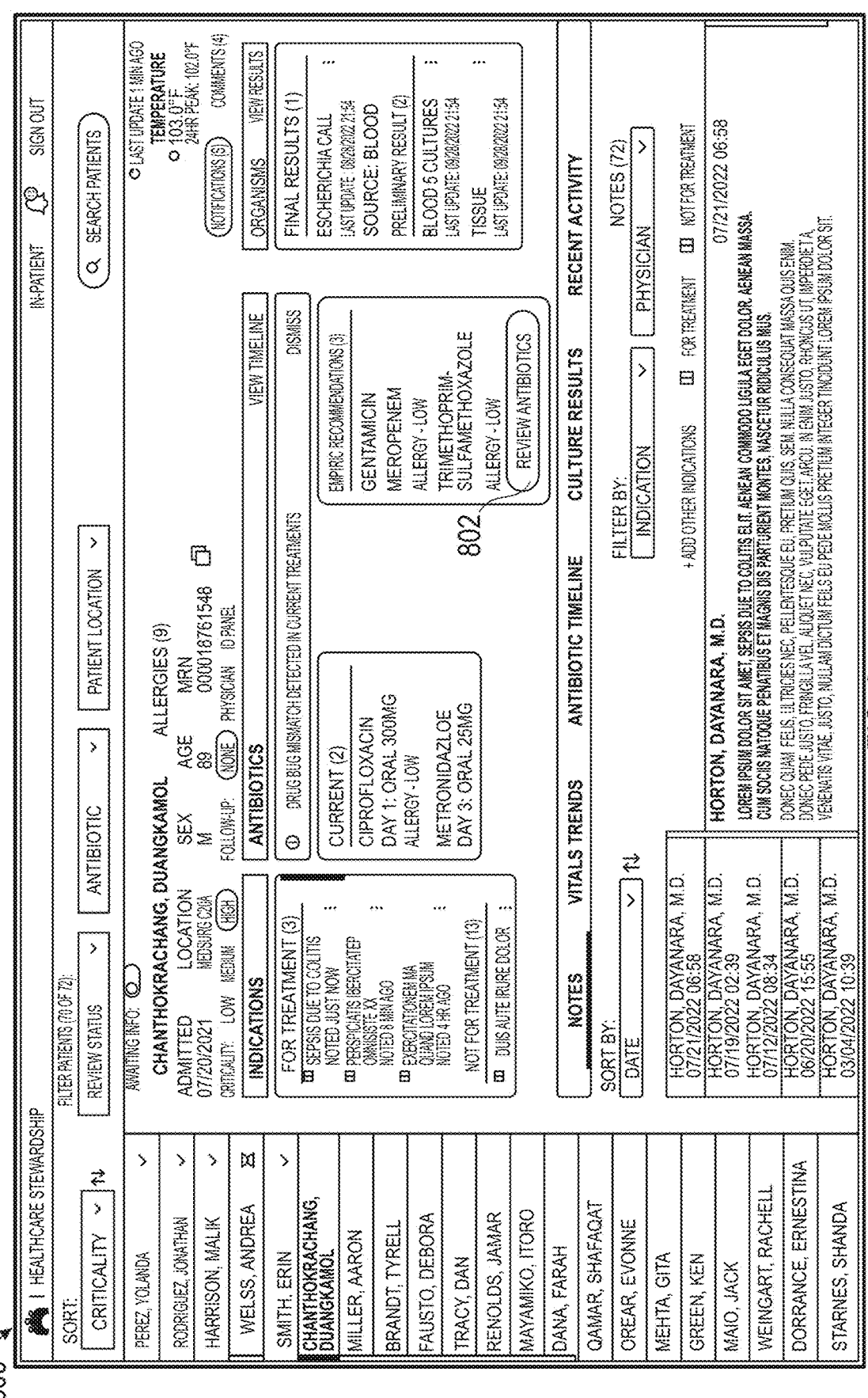

FIG. 8 shows a graphical representation 800 of a user interface for a homepage centralizing patient member information from disparate data sources on a single clinical and care dashboard.

Figure 9:
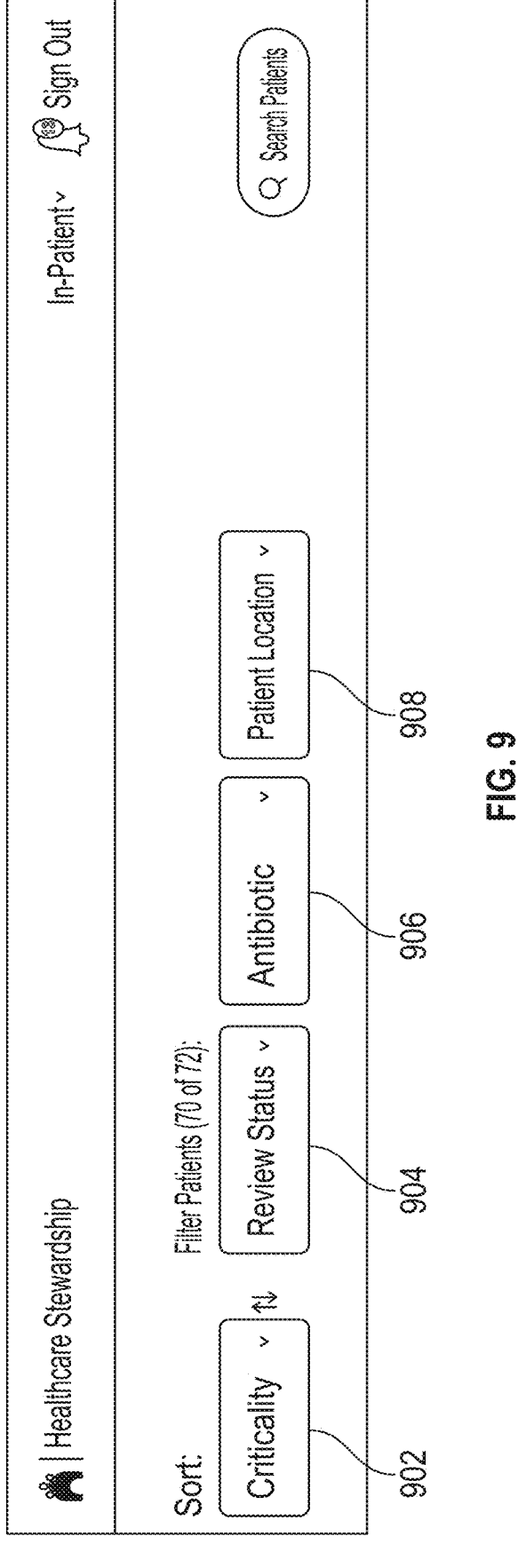

FIG. 9 shows a close-up of a top ribbon of the graphical representation 800 from FIG. 8. In FIG. 9, the close-up of a top ribbon of the graphical representation 800 includes a sort and filter section for reviewing patient member information. The healthcare personnel may sort a criticality of a plurality of patient members by toggling the 'Criticality' button 902 up or down. The healthcare personnel may filter the plurality of patients by interacting with the 'Review Status' button 904, the 'Antibiotic' button 906, and the 'Patient Location' button 908. For example, the healthcare personnel may select the 'Review Status' button 904 to filter the plurality of patient members to surface the patient members who are yet to be reviewed by the healthcare personnel. In another example, the healthcare personnel may select the 'Antibiotic' button 904 to filter the plurality of patient members who were administered with a broad spectrum antibiotic medication. In another example, the healthcare personnel may select the 'Patient Location' button 908 to filter the plurality of patient members by location.

Figure 10:
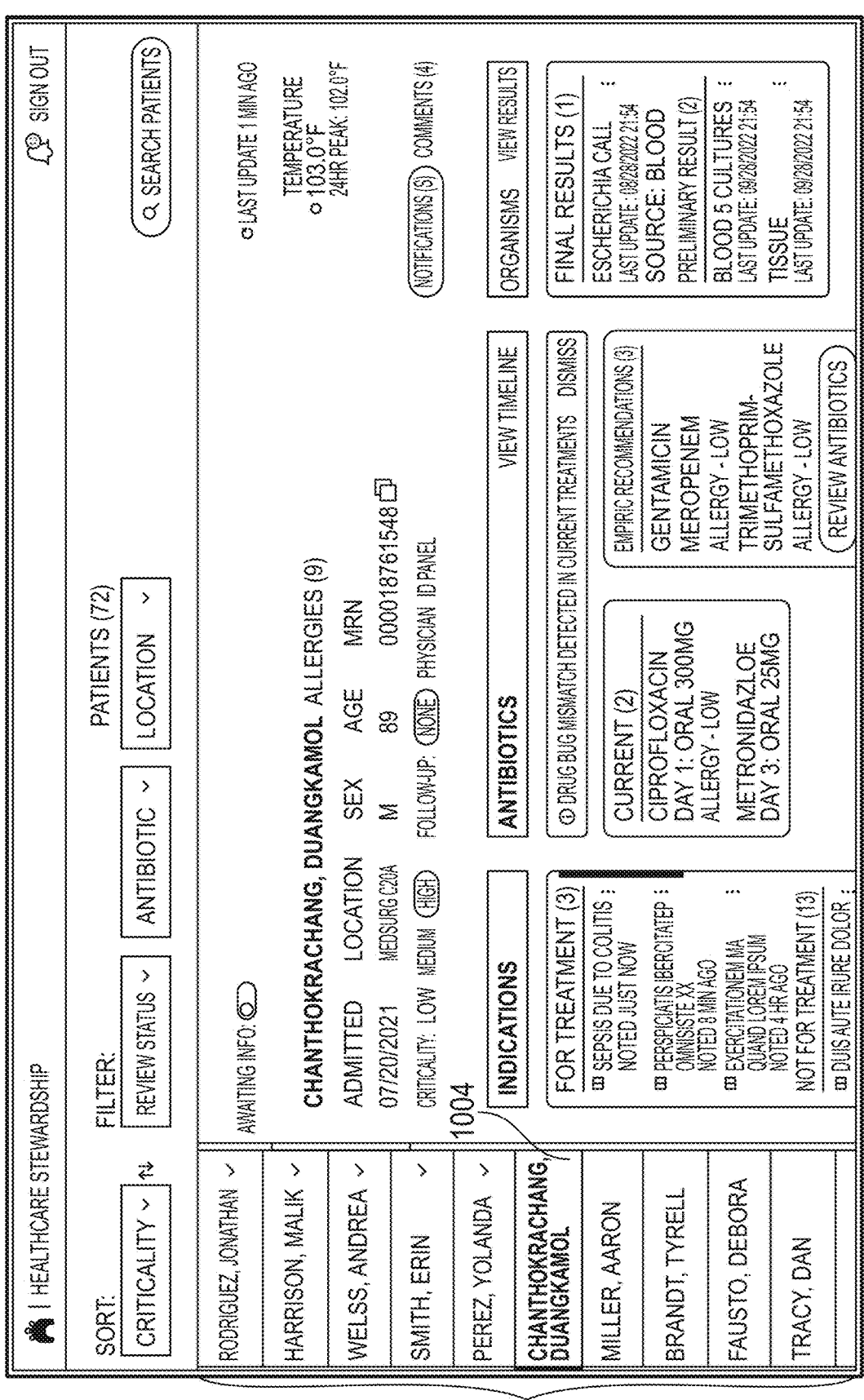

FIG. 10 shows a top portion of the graphical representation 800 from FIG. 8. In FIG. 10, the graphical representation 800 filters and ranks the plurality of patient members on the left panel 1002 based on the search criteria entered in FIG. 9. For example, the left panel 1002 ranks the patient members based on their criticality level. That is, the highly critical patient members may be automatically pushed to the top of the panel 1002 for a healthcare personnel to review. The healthcare personnel may select a patient member 1004 to view their information on the care and clinical dashboard.

Figure 11:
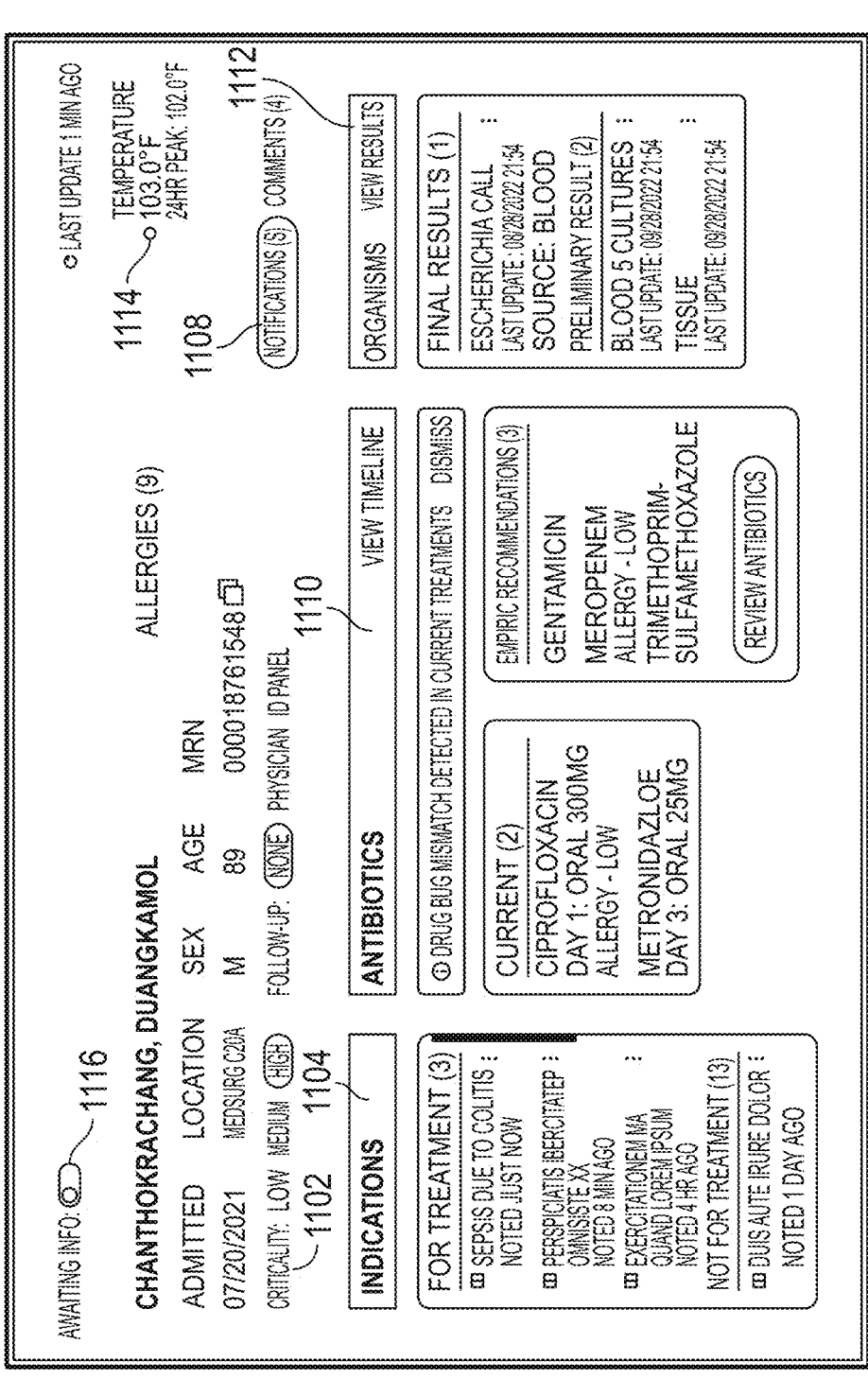

FIG. 11 shows a close up of the patient information retrieved and displayed on the graphical representation 800 based on the selection in FIG. 10. The patient information in the care and clinical dashboard may indicate the criticality level of the selected patient member as output by the trained machine learning models 326. The healthcare personnel may provide their feedback on the criticality level by changing the criticality level based on their personal assessment of the patient information on the care and clinical dashboard. For example, the criticality level of the patient member may be changed from 'HIGH' to 'MEDIUM' or 'LOW' by the healthcare personnel upon their personal assessment. In FIG. 11, the graphical representation 800 shows several sections, such as the indications 1104 retrieved from physician notes using NLP, the antibiotics 1110 usage, and laboratory results 1112 in association with the patient member. The indications 1104 section separates the primary indications (for treatment) and secondary indications (not for treatment). The antibiotics 1110 section shows the currently prescribed antibiotics by the physician and a recommendation of an antibiotics prescription change generated by a trained machine learning model 326 because of a drug bug mismatch detected in the current antibiotics treatment. The laboratory results 1112 section shows the preliminary results and the final results of the bacteria culture test done for the patient member. A healthcare personnel may review the laboratory results 1112, the vitals 1114, the recommended antibiotics, and either agree or disagree with the recommendation. Additionally, the healthcare personnel may select the notifications 1108 to review the new notifications recommended by the trained machine learning model 326 based on updates received in the patient member's information. Alternatively, the healthcare personnel may toggle the 'Awaiting Info' button 1116 to tag and track the patient information to be on top of their care delivery workflow. When the 'Awaiting Info' button 1116 is toggled on, the healthcare personnel gets intelligently notified of the changes in the patient member's information that gets aggregated and filtered from disparate sources.

FIG. 12 shows a bottom portion of the graphical representation 800 from FIG. 8. In FIG. 12, the graphical representation 800 aggregates patient member's information under subsections for an easy review process by the healthcare personnel that reduces their cognitive burden. The graphical representation 800 includes the 'Notes' section 1202 where the annotations in the physician notes are retrieved and presented. The 'Notes' section 1202 includes indications 1204 that are highlighted and user-selectable. When the healthcare personnel selects the indications 1204, the graphical representation 800 may direct to the location in the physician notes where the indications 1204 were retrieved from for evidentiary support. Furthermore, the healthcare personnel may filter the notes 1202 by indication tab 1206, date 1212, and/or physician tab 1208. The left panel 1210 lists all the physicians who have had an encounter with the patient member and provided notes from their encounter.

Figure 13:
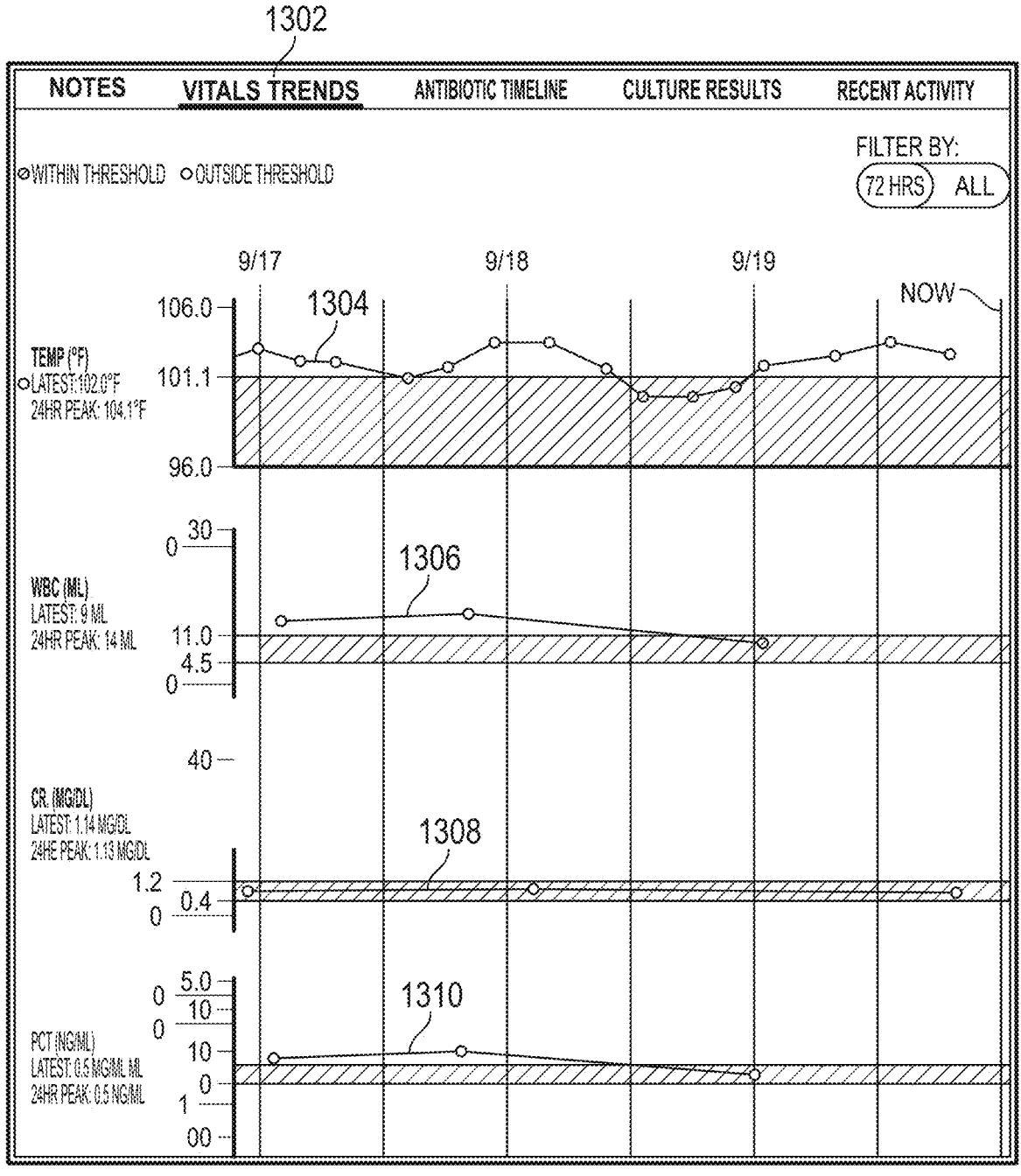

FIG. 13 shows the graphical representation 800 including the subsection 'Vitals Trends' 1302 where the patient member's vitals and their corresponding clinical thresholds are tracked for the healthcare personnel to review. For instance, the 'Vitals Trends' 1302 includes individual graphs plotting the body temperature 1304, the white blood count (WBC) 1306, the creatinine level 1308, and the procalcitonin (PCT) level 1310. The 'Vitals Trends' 1302 may also be filtered by time periods, such as 1 hour, 6 hours, 24 hours, 48 hours, 72 hours, etc. The individual graphs may also visually and distinctly denote which of the measured vitals data points were within and outside the clinical thresholds.

Figure 14:
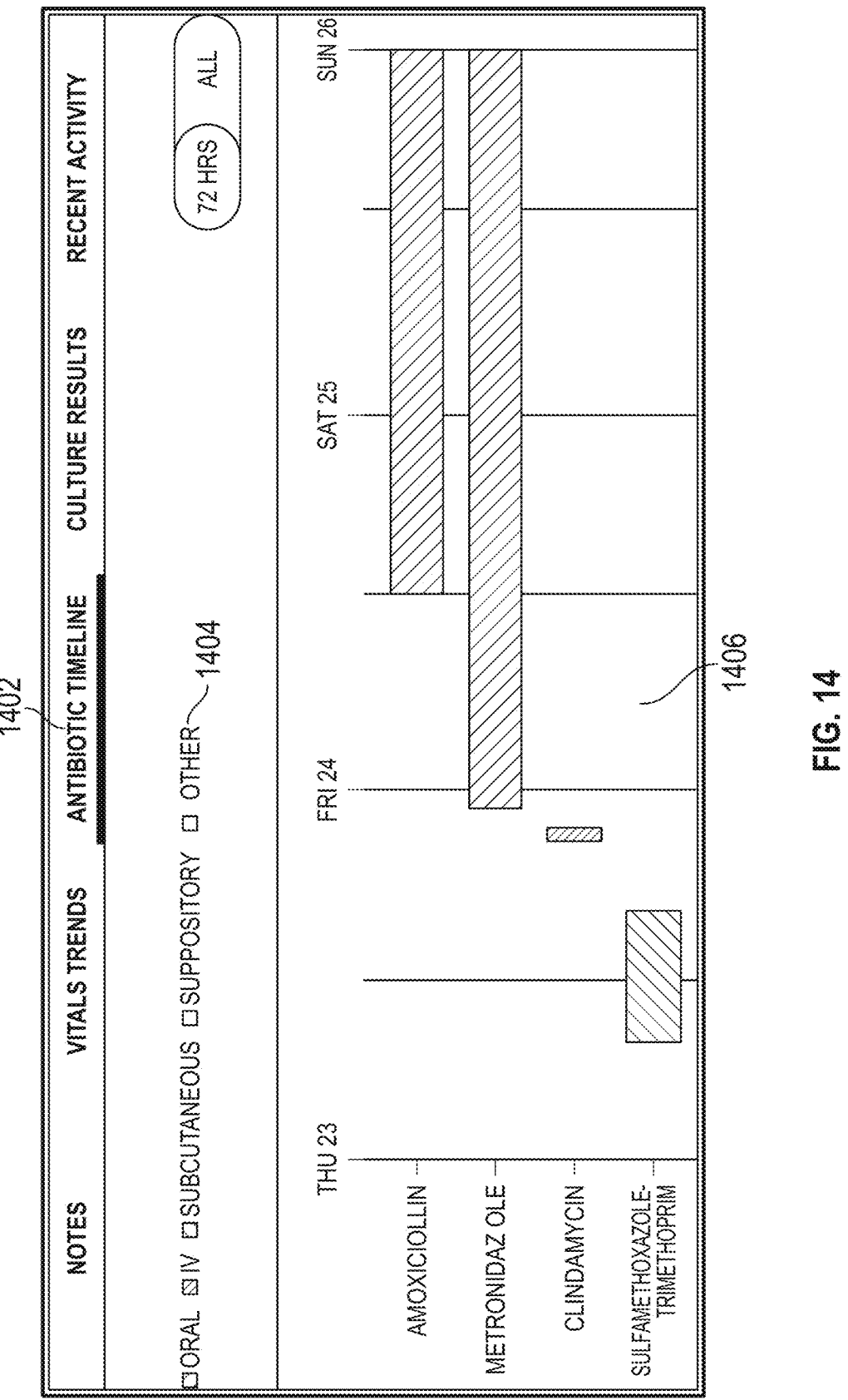

FIG. 14 shows the graphical representation 800 including the subsection 'Antibiotics Timeline' 1402 where the different antibiotics administered to the patient member are tracked and plotted for the healthcare personnel to review. This information is extracted from the physician notes, nurse practitioner's patient round records, and pharmacy order data. For instance, the 'Antibiotics Timeline' 1402 includes a timeline graph 1406 that shows the break-up of the types of antibiotics administered to the patient member over a defined period of time. The 'Antibiotics Timeline' 1402 also conveniently highlights the mode 1404 of drug delivery to the patient member using different colors. The 'Antibiotics Timeline' 1402 may also be filtered by time periods, such as 1 hour, 6 hours, 24 hours, 48 hours, 72 hours, etc.

FIG. 15 shows the graphical representation 800 including the subsection 'Culture Results' 1502 where the preliminary and final results of the bacteria culture tests are displayed for the healthcare personnel to review. The 'Culture Results' 1502 may be filtered by the 'Source' tab 1508 and the 'Status' tab 1510. For example, the 'Source' tab 1508 identifies the sample (blood, tissue, sputum, etc.) that was collected and tested and the 'Status' 1510 identifies the preliminary and the final results of those tests. The healthcare personnel may select the tab 1504 for 'Blood' test on the left panel showing the different test results and view the results 1506 in the right panel. The results 1506 include the susceptible antimicrobials and the resistant antimicrobials identified in the culture test.

FIG. 16 shows the graphical representation 800 including the subsection 'Recent Activity' 1602 where a complete log of recent user activities pertaining to the care delivery workflow of the patient member are tracked for audit purposes. The auditor may filter the 'Recent Activity' 1602 by 'Activity Type' tab 1620, 'Clinician Type' tab 1622, and/or 'Patient Location' tab 1624. For instance, the 'Recent Activity' 1602 tracks several user activities relating to comments 1606, alert notifications 1608, antibiotics updated and approved 1610, patient reviewed 1612, updates entered 1614, indications reviewed 1616, drug-bug mismatch notification 1618, etc.

Figure 17:
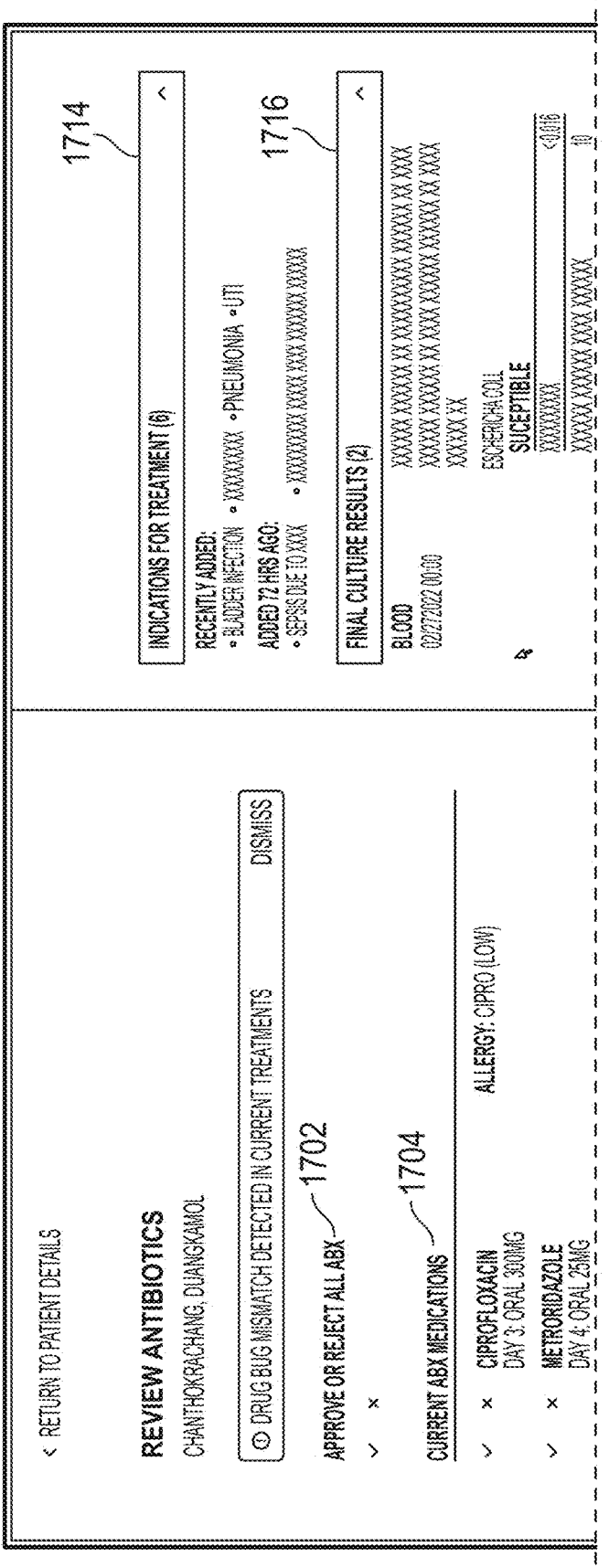

FIG. 17 shows the graphical representation 1700 including a review page where the healthcare personnel reviews the recommendation and provides their feedback. The graphical representation 1700 in FIG. 17 is retrieved and displayed when the healthcare personnel selects the 'Review Antibiotics' button in FIG. 8. The healthcare personnel may review the 'Indications for Treatment' 1714, the 'Final Culture Results' 1716, and 'The Preliminary Results' 1718 on the right. The healthcare personnel may then review and provide their feedback under the 'Current ABX Medications' 1704 that the patient is currently prescribed and the 'Empiric Recommendations' 1706 that is suggested for the healthcare personnel to consider instead. The healthcare personnel may also provide their feedback under 'Approve or Reject all ABX' 1702. If the healthcare personnel disagrees with the 'Empiric Recommendations' 1706, they may add their own prescription antibiotic by selecting 'Add Antibiotic' button 1708. The healthcare personnel may also choose to send the patient's case and the recommendation to a physician or an infectious disease (ID) panel for review by toggling the 'Further Review' button 1710. The healthcare personnel may finish their review by selecting the 'Submit' button 1712. The prescription medication approved by the healthcare personnel during their review is then administered to the patient.

FIG. 18 is a flow diagram illustrating one implementation of another example method 1800 for generating a recommendation for augmenting a stewardship workflow. At 1802, the care augmentation application 110 receives a plurality of clinical care dataset, historical care dataset, and regional care pathway dataset associated with a plurality of patients in a healthcare stewardship program. For example, the healthcare stewardship program may be an antibiotics stewardship program. At 1804, the care augmentation application 110 trains a machine learning model using the plurality of the clinical care dataset, the historical care dataset, and the regional care pathway dataset. The plurality of the clinical care dataset, the historical care dataset, and the regional care pathway dataset may include known care events of interest, patient criticality levels, and patient care treatments to train the machine learning model. At 1806, the care augmentation application 110 receives an input of clinical care data, historical care data, and regional care pathway data associated with a patient from the plurality of patients. For example, the clinical care data may include clinical encounter data, laboratory data, pharmacy data, a combination thereof, etc. The historical care data may include a history of patient care, such as one or more episodes of care associated with the patient. The regional care pathway data may include empirical guidelines, care plans, stewardship workflows, clinical research, clinical studies, etc. implemented in different region, sub region, medical centers, county, state, country, etc. associated with the patient and their cohorts. At 1808, the car augmentation application 110 determines a first output of a patient criticality level, a second output of a care event of interest, and a third output of a recommendation of a treatment based on the input. In one example, the machine learning model may be a neural network that assigns a weight to each of the clinical care data, the historical care data, and the regional care pathway data associated with the patient. At 1810, the care augmentation application 110 automatically surfaces the recommendation of the treatment for review by a healthcare personnel within a workflow of the healthcare stewardship program. For example, a physician may review the recommendation and approve the treatment for administration to the patient. At 1812, the care augmentation application 110 administers the treatment to the patient responsive to the review by the healthcare personnel.

A system and method for facilitating a member journey through healthcare service by augmenting stewardship across multiple service areas has been described. In the above description, for purposes of explanation, numerous specific details are set forth in order to provide a thorough understanding of the techniques introduced above. It will be apparent, however, to one skilled in the art that the techniques can be practiced without these specific details. In other instances, structures and devices are shown in block diagram form in order to avoid obscuring the description and for ease of understanding. For example, the techniques are described in one implementation above primarily with reference to software and particular hardware. However, the present invention applies to any type of computing system that can receive data and commands, and present information as part of any peripheral devices providing services.

Reference in the specification to "one implementation" or "an implementation" means that a particular feature, structure, or characteristic described in connection with the implementation is included in at least one implementation. The appearances of the phrase "in one implementation" in various places in the specification are not necessarily all referring to the same implementation.

Some portions of the detailed descriptions described above are presented in terms of algorithms and symbolic representations of operations on data bits within a computer memory. These algorithmic descriptions and representations are, in some circumstances, used by those skilled in the data processing arts to convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing", "computing", "calculating", "determining", "displaying", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer readable storage medium, such as, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of a hardware implementation, a software implementation, or implementations containing both hardware and software elements. For instance, the technology may be implemented in software, which includes but is not limited to firmware, resident software, microcode, etc. Furthermore, the technology can take the form of a computer program product accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats.

Furthermore, the modules, routines, features, attributes, methodologies, engines, and other aspects of the disclosure can be implemented as software, hardware, firmware, or any combination of the foregoing. Also, wherever an element, an example of which is a module, of the specification is implemented as software, the element can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment. Accordingly, the disclosure is intended to be illustrative, but not limiting, of the scope of the subject matter set forth in the following claims.

What is claimed is:

1. A computer-implemented method comprising:

receiving a set of clinical care dataset, historical care dataset, and regional care pathway dataset associated with a plurality of patients in a healthcare stewardship program;

training a machine learning model using the set of the clinical care dataset, the historical care dataset, and the regional care pathway dataset, the set of the clinical care dataset, the historical care dataset, and the regional care pathway dataset including known care events of interest, patient criticality levels, and patient care treatments to train the machine learning model, the machine learning model including a neural network that learns a corresponding weight to assign to each one of clinical care data, historical care data, and regional care pathway data of different patients for generating a prediction of care events of interest, patient criticality levels, and patient care treatments as outputs;

receiving an input of clinical care data, historical care data, and regional care pathway data associated with a patient from the plurality of patients;

determining, using the machine learning model and the input of clinical care data, historical care data, and regional care pathway data associated with the patient, a first output of a patient criticality level, a second output of a care event of interest associated with the patient criticality level, and a third output of a recommendation of a treatment associated with the patient criticality level and the care event of interest;

receiving, via a secure portal provided by a machine learning module, feedback correcting one or more of the first output of the patient criticality level, the second output of the care event of interest, and the third output of the recommendation of the treatment;

updating, by the machine learning module, identification hints for one or more of the known care events of interest, patient criticality levels, and patient care treatments in the set of clinical care dataset, the historical care dataset, and the regional care pathway dataset based on the feedback;

retraining, by the machine learning module, the machine learning model using the updated identification hints for one or more of the known care events of interest, patient criticality levels, and patient care treatments in the set of clinical care dataset, the historical care dataset, and the regional care pathway dataset;

determining, using the retrained machine learning model and the input of clinical care data, historical care data, and regional care pathway data associated with the patient, a fourth output of a patient criticality level, a fifth output of a care event of interest associated with the patient criticality level, and a sixth output of a recommendation of a treatment associated with the patient criticality level and the care event of interest, the retrained machine learning model assigning a corresponding weight to each one of the input of the clinical care data, the historical care data, and the regional care pathway data associated with the patient in determining the third output of the patient criticality level, the fourth output of the care event of interest, and the sixth output of the recommendation of the treatment, the recommendation of the treatment including timely transitioning of medication from a broad-spectrum to a narrow-spectrum, from a first dosage to a second dosage, and from a first route of administering the medication to a second route of administering the medication;

automatically surfacing the recommendation of the treatment for review by a healthcare personnel within a workflow of the healthcare stewardship program based on the fourth output, the fifth output, and the sixth output of the retrained machine learning model; and administering the treatment including timely transitioning of the medication from the broad-spectrum to the narrow-spectrum, from the first dosage to the second dosage, and from the first route of administering the medication to the patient to the second route of administering the medication to the patient responsive to the review by the healthcare personnel.

2. The computer-implemented method of claim 1, further comprising:

filtering the clinical care data, the historical care data, and the regional care pathway data associated with the patient;

generating a clinical dashboard based on the filtering, the first output of the patient criticality level, the second output of the care event of interest, and the third output of the recommendation of the treatment; and presenting the clinical dashboard to the healthcare personnel within the workflow of the healthcare stewardship program.

3. The computer-implemented method of claim 2, further comprising:

generating an alert notification of the care event of interest; and automatically surfacing, via the clinical dashboard, the alert notification of the care event of interest for review by the healthcare personnel.

4. The computer-implemented method of claim 2, further comprising:

generating a listing of the plurality of patients in the clinical dashboard;

sorting the patient in the listing of the plurality of patients based on the patient criticality level; and associating a graphical indicator with the patient in the listing of the plurality of patients, the graphical indicator indicating a status associated with a review of the patient by the healthcare personnel within the workflow of the healthcare stewardship program.

5. The computer-implemented method of claim 2, further comprising:

receiving, via the clinical dashboard, a feedback from the healthcare personnel on the first output of the patient criticality level, the second output of the care event of interest, and the third output of the recommendation of the treatment;

updating the plurality of the clinical care dataset, the historical care dataset, and the regional care pathway dataset based on the feedback; and retraining the machine learning model using the updated plurality of the clinical care dataset, the historical care dataset, and the regional care pathway dataset.

6. The computer-implemented method of claim 5, wherein the feedback includes at least one from a group of acceptance, rejection, and correction.

7. The computer-implemented method of claim 2, wherein the clinical dashboard includes healthcare personnel notes, patient vitals trend, patient medication timeline, patient laboratory results, and an activity log associated with the treatment of the patient within the workflow of the healthcare stewardship program.

8. The computer-implemented method of claim 1, wherein the patient criticality level is one from a group of low, medium, and high.

9. The computer-implemented method of claim 1, wherein the treatment includes a therapeutic procedure, a surgical procedure, a non-surgical procedure, a laboratory test, a medical test, an imaging test, a medication prescription, and a follow-up care.

10. The computer-implemented method of claim 1, wherein the machine learning model includes a convolutional neural network assigning a weight to each of the clinical care data, the historical care data, and the regional care pathway data associated with the patient.

11. The computer-implemented method of claim 1, wherein the healthcare stewardship program is an antibiotics stewardship program.

12. A system comprising:

one or more processors; and a memory, the memory storing instructions, which when executed cause the one or more processors to:

receive a set of clinical care dataset, historical care dataset, and regional care pathway dataset associated with a plurality of patients in a healthcare steward-ship program;

train a machine learning model using the set of the clinical care dataset, the historical care dataset, and the regional care pathway dataset, the set of the clinical care dataset, the historical care dataset, and the regional care pathway dataset including known care events of interest, patient criticality levels, and patient care treatments to train the machine learning model, the machine learning model including a neu-ral network that learns a corresponding weight to assign to each one of clinical care data, historical care data, and regional care pathway data of different patients for generating a prediction of care events of interest, patient criticality levels, and patient care treatments as outputs;

receive an input of clinical care data, historical care data, and regional care pathway data associated with a patient from the plurality of patients;

determine, using the machine learning model and the input of clinical care data, historical care data, and regional care pathway data associated with the patient, a first output of a patient criticality level, a second output of a care event of interest associated with the patient criticality level, and a third output of a recom-mendation of a treatment associated with the patient criticality level and the care event of interest;

receiving, via a secure portal provided by a machine learning module, feedback correcting one or more of the first output of the patient criticality level, the second output of the care event of interest, and the third output of the recommendation of the treatment;

updating, by the machine learning module, identification hints for one or more of the known care events of interest, patient criticality levels, and patient care treat-ments in the set of clinical care dataset, the historical care dataset, and the regional care pathway dataset based on the feedback;

retraining, by the machine learning module, the machine learning model using the updated identification hints for one or more of the known care events of interest, patient criticality levels, and patient care treatments in the set of clinical care dataset, the historical care dataset, and the regional care pathway dataset;

determining, using the retrained machine learning model and the input of clinical care data, historical care data, and regional care pathway data associated with the patient, a fourth output of a patient criticality level, a fifth output of a care event of interest associated with the patient criticality level, and a sixth output of a recommendation of a treatment associated with the patient criticality level and the care event of interest, the retrained machine learning model assigning a cor-responding weight to each one of the input of the clinical care data, the historical care data, and the regional care pathway data associated with the patient in determining the third output of the patient criticality level, the fourth output of the care event of interest, and the sixth output of the recommendation of the treat-ment, the recommendation of the treatment including timely transitioning of medication from a broad-spec-trum to a narrow-spectrum, from a first dosage to a second dosage, and from a first route of administering the medication to a second route of administering the medication;

automatically surface the recommendation of the treat-ment for review by a healthcare personnel within a workflow of the healthcare stewardship program based on the fourth output, the fifth output, and the sixth output of the retrained machine learning model; and administer the treatment including timely transitioning of the medication from the broad-spectrum to the narrow-spectrum, from the first dosage to the second dosage, and from the first route of administering the medication to the patient to the second route of administering the medication to the patient responsive to the review by the healthcare personnel.

13. The system of claim 12, wherein the instructions further cause the one or more processors to:

filter the clinical care data, the historical care data, and the regional care pathway data associated with the patient;

generate a clinical dashboard based on the filtering, the first output of the patient criticality level, the second output of the care event of interest, and the third output of the recommendation of the treatment; and present the clinical dashboard to the healthcare personnel within the workflow of the healthcare stewardship program.

14. The system of claim 13, wherein the instructions further cause the one or more processors to:

generate an alert notification of the care event of interest; and automatically surface, via the clinical dashboard, the alert notification of the care event of interest for review by the healthcare personnel.

15. The system of claim 13, wherein the instructions further cause the one or more processors to:

generate a listing of the plurality of patients in the clinical dashboard;

sort the patient in the listing of the plurality of patients based on the patient criticality level; and associate a graphical indicator with the patient in the listing of the plurality of patients, the graphical indi-cator indicating a status associated with a review of the patient by the healthcare personnel within the workflow of the healthcare stewardship program.

16. The system of claim 13, wherein the instructions further cause the one or more processors to:

receive, via the clinical dashboard, a feedback from the healthcare personnel on the first output of the patient criticality level, the second output of the care event of interest, and the third output of the recommendation of the treatment;

update the plurality of the clinical care dataset, the his-torical care dataset, and the regional care pathway dataset based on the feedback; and retrain the machine learning model using the updated plurality of the clinical care dataset, the historical care dataset, and the regional care pathway dataset.

17. The system of claim 16, wherein the feedback includes at least one from a group of acceptance, rejection, and correction.

18. The system of claim 13, wherein the clinical dash-board includes healthcare personnel notes, patient vitals trend, patient medication timeline, patient laboratory results, and an activity log associated with the treatment of the patient within the workflow of the healthcare stewardship program.

19. The system of claim 12, wherein the patient criticality level is one from a group of low, medium, and high.

20. The system of claim 12, wherein the treatment includes a therapeutic procedure, a surgical procedure, a non-surgical procedure, a laboratory test, a medical test, an imaging test, a medication prescription, and a follow-up care.

\* \* \* \* \*